(12) United States Patent
Oberländer et al.

(10) Patent No.: US 10,390,811 B2
(45) Date of Patent: Aug. 27, 2019

(54) DEVICE FOR PROVIDING AN ACCESS OPENING IN A BODY, IN PARTICULAR FOR A SPINAL OPERATION

(71) Applicant: Karl Storz GmbH & Co. KG, Tuttlingen (DE)

(72) Inventors: Martin Oberländer, Engen (DE); Roland E. Stark, Uhldingen-Mühlhofen (DE)

(73) Assignee: Karl Storz SE Co. & KG, Tuttlingen (DE)

( * ) Notice: Subject to any disclaimer, the term of this patent is extended or adjusted under 35 U.S.C. 154(b) by 795 days.

(21) Appl. No.: 14/285,244

(22) Filed: May 22, 2014

(65) Prior Publication Data

US 2014/0350346 A1    Nov. 27, 2014

(30) Foreign Application Priority Data

May 22, 2013   (DE) .................. 10 2013 209 413

(51) Int. Cl.
*A61B 17/02* (2006.01)
*A61B 17/34* (2006.01)
(Continued)

(52) U.S. Cl.
CPC ...... *A61B 17/0218* (2013.01); *A61B 1/00154* (2013.01); *A61B 1/3132* (2013.01);
(Continued)

(58) Field of Classification Search
CPC ... A61B 17/0218; A61B 17/025; A61B 90/36; A61B 17/3421; A61B 1/0661; A61B 1/0669
(Continued)

(56) References Cited

U.S. PATENT DOCUMENTS 3,075,516 A * 1/1963 Strauch .................. A61B 1/32
                                                    600/184
4,211,215 A   7/1980 Heine et al.
(Continued)

FOREIGN PATENT DOCUMENTS

AT        71385 B       3/1916
DE     2738203 C2      10/1979
(Continued)

OTHER PUBLICATIONS

Search Report issued for European patent application No. 14169280.6 dated Nov. 6, 2014, with machine English translation, 17 pages.
German Search Report issued for German Patent Application No. 10 2013 209 413.2 dated Mar. 7, 2014, with machine English translation, 9 pages.

*Primary Examiner* — Si Ming Ku
(74) *Attorney, Agent, or Firm* — Prince Lobel Tye LLP

(57) ABSTRACT

A device for providing an access opening in a body, in particular for a spinal operation, comprised of a tubular device body (12) that extends along a longitudinal axis (L) of a device body, said body having a distal end (14) that is to be positioned inside a body and a proximal end (16) that is to be positioned outside a body, wherein in the region of the proximal end (16) an optics-carrier arrangement (28) with a movable optics-carrier (36) is positioned or can be positioned to have a path of motion (B) about the longitudinal axis of the device body, characterized in that that the optics carrier arrangement (28) comprises a guideway element (30) that carries the optics carrier (36), said guideway element having a guideway region (34) that can be positioned by means of pivoting about a swivel axis (S) in an operating position in the region of the proximal end (16) of the device body (12).

33 Claims, 19 Drawing Sheets

Figure 1:
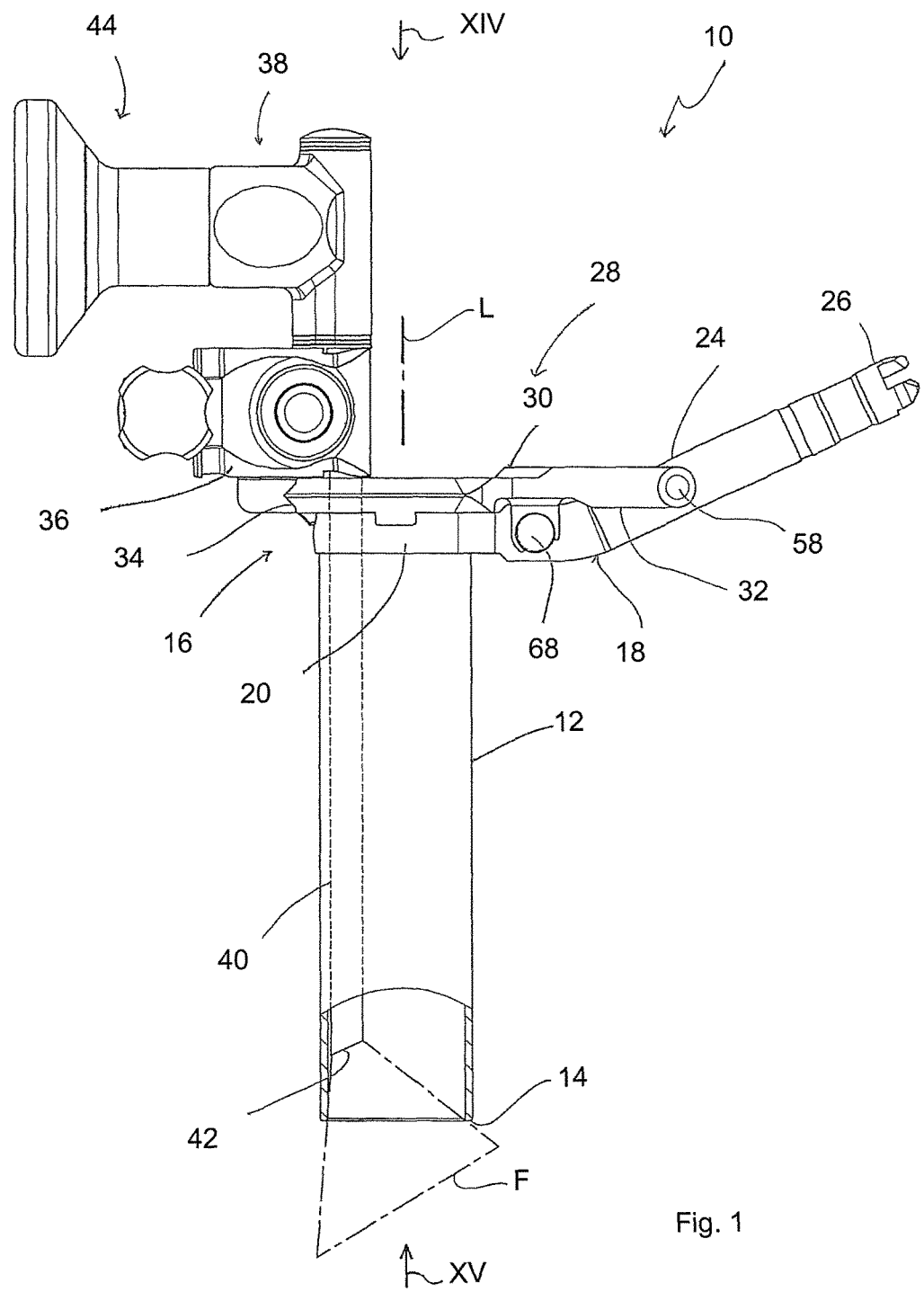

(51) Int. Cl.
  *A61B 1/00* (2006.01)
  *A61B 1/313* (2006.01)
  *A61B 90/57* (2016.01)
  *A61B 17/00* (2006.01)
  *A61B 90/30* (2016.01)

(52) U.S. Cl.
  CPC ........ *A61B 17/025* (2013.01); *A61B 17/3421* (2013.01); *A61B 90/57* (2016.02); *A61B 17/0293* (2013.01); *A61B 2017/00261* (2013.01); *A61B 2017/0225* (2013.01); *A61B 2017/0256* (2013.01); *A61B 2017/347* (2013.01); *A61B 2017/3445* (2013.01); *A61B 2090/306* (2016.02)

(58) Field of Classification Search
  USPC ....... 600/201, 204, 213, 223, 227–234, 245, 600/241, 248
  See application file for complete search history.

(56) References Cited

U.S. PATENT DOCUMENTS

| | | | |
|---|---|---|---|
| 6,152,871 | A | 11/2000 | Foley et al. |
| 7,691,120 | B2 * | 4/2010 | Shluzas .............. A61B 17/3439 600/219 |
| 9,107,650 | B2 | 8/2015 | Bjork et al. |
| 9,480,472 | B2 | 11/2016 | Bjork et al. |
| 2003/0055437 | A1 * | 3/2003 | Yasunaga ........... A61B 1/00149 606/130 |

FOREIGN PATENT DOCUMENTS

| | | |
|---|---|---|
| DE | 29916026 U1 | 11/1999 |
| DE | 69922030 T2 | 11/2005 |
| EP | 1 192 905 A1 | 4/2002 |
| EP | 1466564 A1 | 10/2004 |
| EP | 1 649 623 A1 | 4/2006 |
| EP | 1723918 A1 | 11/2006 |
| EP | 1 466 564 B1 | 10/2010 |

* cited by examiner

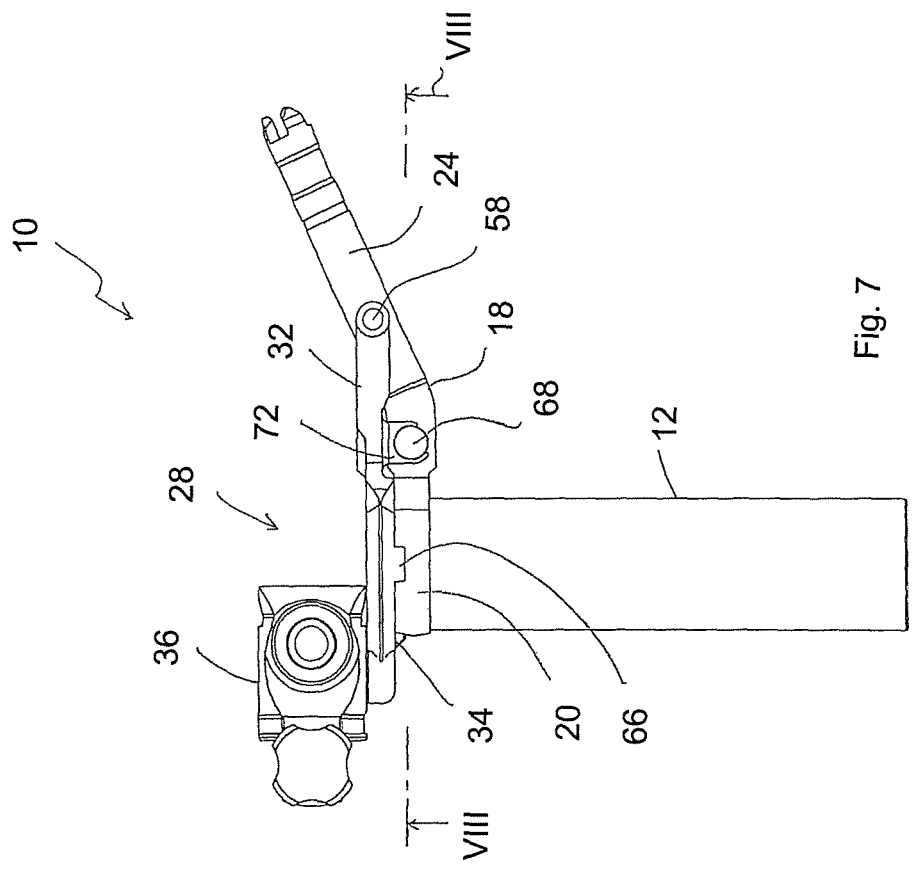
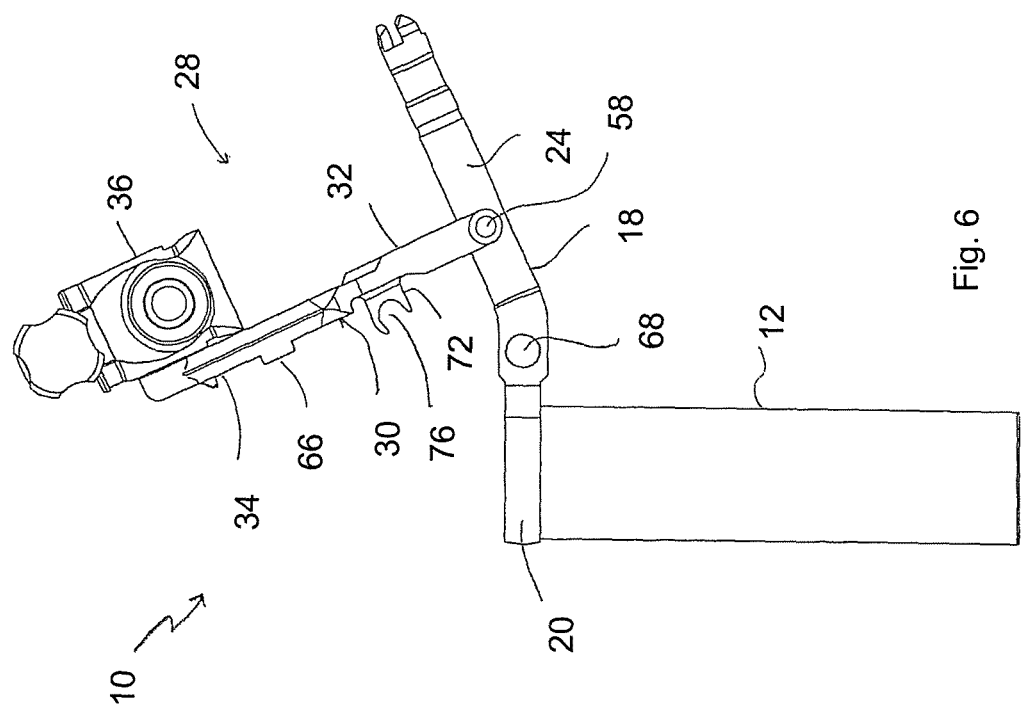
Fig. 7
Fig. 6

DEVICE FOR PROVIDING AN ACCESS OPENING IN A BODY, IN PARTICULAR FOR A SPINAL OPERATION

CROSS REFERENCE TO RELATED APPLICATION(S)

This application claims priority to German patent application no. DE 10 2013 209 413.2, which was filed on May 22, 2013, the entire contents of which are incorporated herein by reference.

The present invention relates to a device for providing an access opening in a body, in particular for a spinal operation, comprised of a tubular device body that extends along a longitudinal axis of a device body, said body having a distal end that is to be positioned inside a body and a proximal end that is to be positioned outside a body, wherein in the region of the proximal end, an optics-carrier arrangement with a movable optics-carrier is positioned or can be positioned with a path of motion about the longitudinal axis of the device body.

A device for performing percutaneous operations, for example in the region of the lumbar vertebrae or in the region of the cervical vertebrae of a human body, is known from EP 1 466 564 B1. This known device is comprised of a substantially cylindrical device body extending longitudinally along a longitudinal axis of a device body. At a distance from the proximal end of this device body, an arm-like carrier for securing the device body to an adjustable stand or the like is attached to the device body, said carrier extending laterally away from the device body. In order to attach an optics system to the device body, a sleeve-like optics carrier is slid onto the device body at its proximal end, so that this optics carrier substantially extends between the arm-like carrier that extends laterally away from the device body and the proximal end of the device body. The optics carrier, with the optics system affixed to it, can be moved about a longitudinal device axis in a substantially circular path of motion.

The object of the present invention is to provide an access opening in a body, in particular for the performance of a spinal operation, which, with a design that is easy to use and functions reliably, enables positioning of the proximal end of the device body, and thus the optics carrier and the optics system affixed to it, close to a body surface.

This object is inventively achieved with a device for providing an access opening in a body, in particular for a spinal operation, which comprises a tubular device body that extends along a device-body axis, with a distal end that is to be positioned inside a body and a proximal end that is to be positioned outside a body, wherein in the region of the proximal end, an optics-carrier arrangement with a movable optics-carrier is positioned or can be positioned with a path of motion about the longitudinal axis of the device body.

Thereby it is also provided that the optics arrangement comprises a guideway element that carries the optics carrier, said guideway element having a guideway region that can be positioned in an operating position at the proximal end of the device body by pivoting around a swivel axis.

Whereas with the design of the optics carrier known from the prior art, the optics carrier is slid onto the device carrier in the region of the proximal end of the device carrier, and thus this longitudinal region of the device body which is overlapped by the optics carrier must remain outside the body that is to be treated, with the inventive design, a guideway element is provided on which the optics carrier is carried for the purpose of movement about the longitudinal axis of the device body. This guideway element is subsequently positioned, by means of a swiveling movement, at the proximal end of the device body, i.e. is not necessarily slid over a larger longitudinal region of the device body in the region of the proximal end of same. This allows for deeper immersion of the device body in the body that is to be treated, or to ensure that the region of the device body that remains outside the body during a surgical procedure is shorter. In that way, the optics carrier and thus also the optics system carried by it move closer to the body surface, i.e. the skin of the body to be treated.

A defined movement of the optics carrier on the guideway element that carries it can be ensured in that the guideway region is designed in the shape of a ring and has a ring-like first element, preferably a guide groove or guide surface, whereby a second guide element, preferably a guide projection or guide ring of the optics carrier for moving the optics carrier in its path of motion about the longitudinal axis of the device body, is guided along the ring-like first guide element and can be fixed preferably in any position along the first guide element.

In order to ensure both substantial functionalities of the guideway element, namely on the one hand to carry the optics carrier and on the other to provide the swivel mount in relation to the device body, it is proposed that the guideway element also have a swivel/locking region for swivel-mounting and locking of the guideway element in the operating position on a swivel bracket element that extends away from the device body. The swivel bracket element can also be used to attach the device body to an adjustable stand or the like.

In order to firmly attach the swivel bracket element to the device body, it is proposed that the swivel bracket element include a fastening region that preferably circularly encloses the device body and is preferably flush with the proximal end of the device body, and a carrier region that extends away from the fastening region. The positioning of the swivel bracket element very close to the proximal end of the device body, namely such that its fastening region lies flush with the proximal end or with a face side of the device body at the proximal end, is made possible in the inventive design by virtue of the optics carrier per se not having to be slid onto the device body in the region of the proximal end of same, but rather the optics carrier arrangement comprises an assembly especially provided for carrying the optics carrier, namely the guideway element, the guideway region of which can be positioned in the direction of the longitudinal axis of the device body, axially adjacent to the proximal end of the device body. It should be pointed out that that the design of the fastening region being such that it circularly encloses the device body is particularly advantageous, because in this way, with positioning very close to the proximal end of the device body, a stable mount can be achieved, for example by means of welding, gluing, or some other matter of material interpenetration. Alternatively, provision of the fastening region as the end of a rod-like swivel bracket element, and attachment of this end to an outer surface region of the device body by means of welding or gluing would also be possible.

In order to ensure a defined swiveling movement of the guideway element relative to the device body, or of the swivel bracket element provided on the device body, it is proposed that on an assembly of swivel bracket element and swivel/lock region, preferably on the swivel bracket element, at least one swivel lug be provided, and that on the other assembly of swivel bracket element and swivel/lock region, preferably the swivel/lock region of the guideway element, an open swivel recess be assigned in a surrounding area to each swivel lug for insertion of a swivel lug. It should be pointed out here that for purposes of the present invention, an assembly may comprise a number of components or may be assembled from a number of components, but in principle may also be a single-piece component of the device.

Because it is advantageous, in the process of inserting the device body into an incision made in the body to be treated, to have the guideway element with the optics carrier carried thereon detached from the device body or from the swivel bracket element, but still guarantee, after attachment of the guideway element to the swivel bracket element, a relative positioning of these two assemblies relative to one other that precludes detachment, it is further proposed that the at least one swivel lug for insertion into a swivel recess in an insertion-relative position between the swivel/lock region and the swivel bracket element in at least one surrounding region has a smaller cross-sectional dimension than in another surrounding region, whereby, when there is a swivel lug received in a swivel recess, and a swivel/lock region and swivel bracket element are pivoted out of the insertion-relative position with respect to one another, the at least one swivel lug cannot be moved out of the swivel recess.

Defined relative positioning of the guideway element relative to the swivel bracket element during or even after execution of the swivel movement can be further supported in that on the swivel bracket element, two swivel lugs that substantially extend along a common swivel axis are provided, and that the swivel/lock region of the guideway element has a forked design with two forked end regions, and that in each forked end region there is a swivel recess.

Since during the surgical intervention, a stable position secure against undesirable movement of the guideway element relative to the device body is required, it is also proposed that on a swivel bracket element and swivel/lock region assembly, preferably on the swivel bracket element, at least one locking lug is provided, and that on the other swivel bracket element and swivel/lock region assembly, preferably on the swivel/lock region of the guideway element, an open locking recess is assigned in a surrounding region to each locking lug for insertion of a locking lug.

So as to halt or to initiate the locking effect in a simple manner, it can be provided that the at least one locking lug is movable, in the direction of a longitudinal projection axis, between a receiving position for insertion into a locking recess and a locking position, whereby in the locking position a locking section of the locking lug engages an opposing locking section of the locking recess such that the locking lug cannot move out of the locking recess.

Unwanted release of the locked state can be prevented by the at least one locking lug being pre-tensioned (pre-loaded) in its locked position.

The reciprocal locking action between the guideway element and the swivel bracket element can be further improved if two locking lugs extending along a common longitudinal projection axis are provided on the swivel bracket element, and if two locking recess projections, each having one locking recess, are provided on the swivel/lock region of the guideway element.

According to a further particularly advantageous aspect of the present invention, which can be provided in association with one or all of the previous groups of features, but can also develop a particularly advantageous effect as an independent inventive aspect, it can be provided that the optics carrier arrangement include a guideway region that is positioned or can be positioned at the proximal end of the device body, with a first guide element, preferably a guide groove or guide surface, in a guideway region and optics carrier assembly, preferably in the guideway region, and with a second guide element, preferably a guide nut or guide ring, in the other guideway region and optics carrier assembly, preferably the optics carrier, guided on its path of motion about the longitudinal device axis along the first guide element.

Provision of a first guide element, for example a guide groove or guide surface, advantageously in the guideway region or on the device body, and provision of a second guide element, for example a guide projection or guide ring that interacts with this guide element, advantageously on the optics carrier allows on the one hand a compact design that requires a comparatively short axial size, but on the other ensures defined guidance or defined fixation of the optics carrier on the guideway region. In this way the guideway region can of course be positioned in the previously described manner by means of a swivel movement near or adjacent to the proximal end of the device body. Nevertheless, the advantageous interaction, for example between a guide groove and guide projection that engages it can also be achieved when the guideway region is provided in a different way, for example by sliding it on axially or by providing an integral component or a component that is securely attached to the device body.

For engagement of the guide projection, the guide groove is advantageously open in the direction of the longitudinal axis of the device body, away from the proximal end region of the device body. In this way a mutual interference of the optics carrier provided or carried on the guideway region with other system components can be avoided.

In order to prevent the guide projection from moving out of the guide groove, in particular when the optics carrier is not fixed in relation to the guideway region and is moved along the path of motion about the longitudinal axis of the device body, it is proposed that the guide groove have a groove undercut region, and that an undercut engagement region be provided on the guide projection to engage the groove undercut region.

In an alternative embodiment, the first guide element can include a guide surface that circularly encloses the longitudinal axis of the device body, preferably as a closed ring. The second guide element can include a guide ring, wherein the guide ring has an opposing guide surface to come into contact with the guide surface. When in contact with the guide surface, preferably the opposing guide surface also extends substantially completely about the longitudinal axis of the device body, so that between the guideway region and the optics carrier there is not a guide interaction that is limited to a relatively short surrounding region, but rather a circular guide interaction is produced. Due to this circular guide interaction, there is substantially no risk, when the optics system is carried on the optics carrier, of causing a tilt that could affect the movement of the optics carrier along the path of motion. In addition, undercuts that make sterilization more difficult are avoided.

Advantageously, one surface of the guide surface and opposing surface, for example the guide surface, is an inner circumference surface, whereas the other surface, for example the opposing guide surface, can be an outer circumference surface.

In order to achieve an improved guide interaction between the two guide elements on the one hand, while ensuring a defined axial cohesion on the other, it is further proposed that there be a guide counterbore that extends in the direction of the path of motion assigned to one surface of the guide surface and opposing guide surface, and that there be a guide projection extending in the direction of the path of motion assigned to the other surface for engaging the guide borehole.

In order to bring the guide ring with its opposing guide surface into guide interaction with the guideway region or the guide surface provided there, it is proposed that the guide ring be radially elastic. In that way, it is for example possible to radially compress the guide ring for insertion into the guideway region and to release the compression load when a guide ring is inserted in the guideway region, so that the guide ring, due to its radial elasticity, returns to its original form, and thereby, with its opposing guiding surface, comes into guide contact with the guiding surface.

An additionally improved guiding effect for the optics carrier can be achieved in that, in the region of the proximal end of the device body, an additional guide surface that circularly encloses the longitudinal axis of the device body is provided, and that on the guide ring, an additional opposing guide surface is provided for making contact with the additional guide surface.

For stable fixation of the optics carrier in relation to the device body or the guideway region, it is proposed that a guideway region and optics carrier assembly, preferably the optics carrier, is comprised of a fixing component that can be pressed against the other guideway region and optics carrier assembly, preferably the guideway region, for fixing the optics carrier, preferably in any position, along the guide groove relative to the guideway region. As the relative movement between the optics carrier and the guideway region is defined by the first guide element and the second guide element, it is further guaranteed that any desired relative position of the optics carrier along its circular path of motion can be maintained.

When a fixing component is provided that can be pressed, relative to the longitudinal axis of the device body, substantially radially from outside against an abutment region in the guideway region, the optics carrier can be stably fixed relative to the guideway region without impairment of the cross-sectional opening of the tubular device body and thus of the opening made for performance of a surgical intervention.

Thus it is also advantageous if, for effecting and releasing the attachment, the fixing element is substantially radially movable relative to the longitudinal axis of the device body. This ensures that a fixing force impingement occurs substantially orthogonally to the respective local direction of movement of the optics carrier, which ensures equally stable fixation against movement in either direction.

In order to produce or end the fixing effect, it is proposed that a fixing element actuator be assigned to the fixing element for the purpose of switching the fixing element between a fixing position and a release position.

The actuating force that is required to move the fixing element in the direction of a fixing position or in the direction of a release position can be transmitted in a simple but reliable manner in that the fixing element actuator is comprised of a first impingement region that is movable with the fixing element and a second impingement region on an impingement component, which impinges on the first impingement region and can be displaced to move the fixing element relative to the first impingement region, wherein at least one impingement region and preferably each impingement region is designed in the form of a wedge.

Thereby, in order to obtain a compact design, it can be provided that the first impingement region with the fixing element is displaceable in a first direction of displacement, and that the second impingement region with the impingement component is displaceable in a second direction of displacement that is at an angle to the first direction of displacement, preferably substantially orthogonal to it.

The movement of the impingement component that is required for the movement of the fixing element can be effected in a simple manner by having a spindle drive assigned to the impingement component. By means of a spindle drive of this type, a very precise adjustment of the impingement component can be achieved, and thus an equally precise adjustment of the fixing element, whereby, by means of this kind of spindle drive, the forces required to achieve stable fixation can also be provided.

In order to guarantee movement of the fixing element in both possible orientations, i.e. in the direction of the fixing position and in the direction of the release position by means of the two impingement regions that are in impingement interaction, it is further proposed that the first impingement region and the second impingement region be in positive-locking engagement with each other.

In order to attach an optics system to the optics carrier, it is proposed that an optics fixing region be provided on the optics carrier for fixation of an optics system.

In this way a stable but stilly simply produced as well as simply releasable fixation can be achieved in that the optics fixation region has a dovetail interior profile or a dovetail exterior profile, preferably a dovetail interior profile, as well as a movable optics system fixing element on the optics carrier for effecting and releasing fixation of the optics system relative to the optics carrier.

Figure 2:
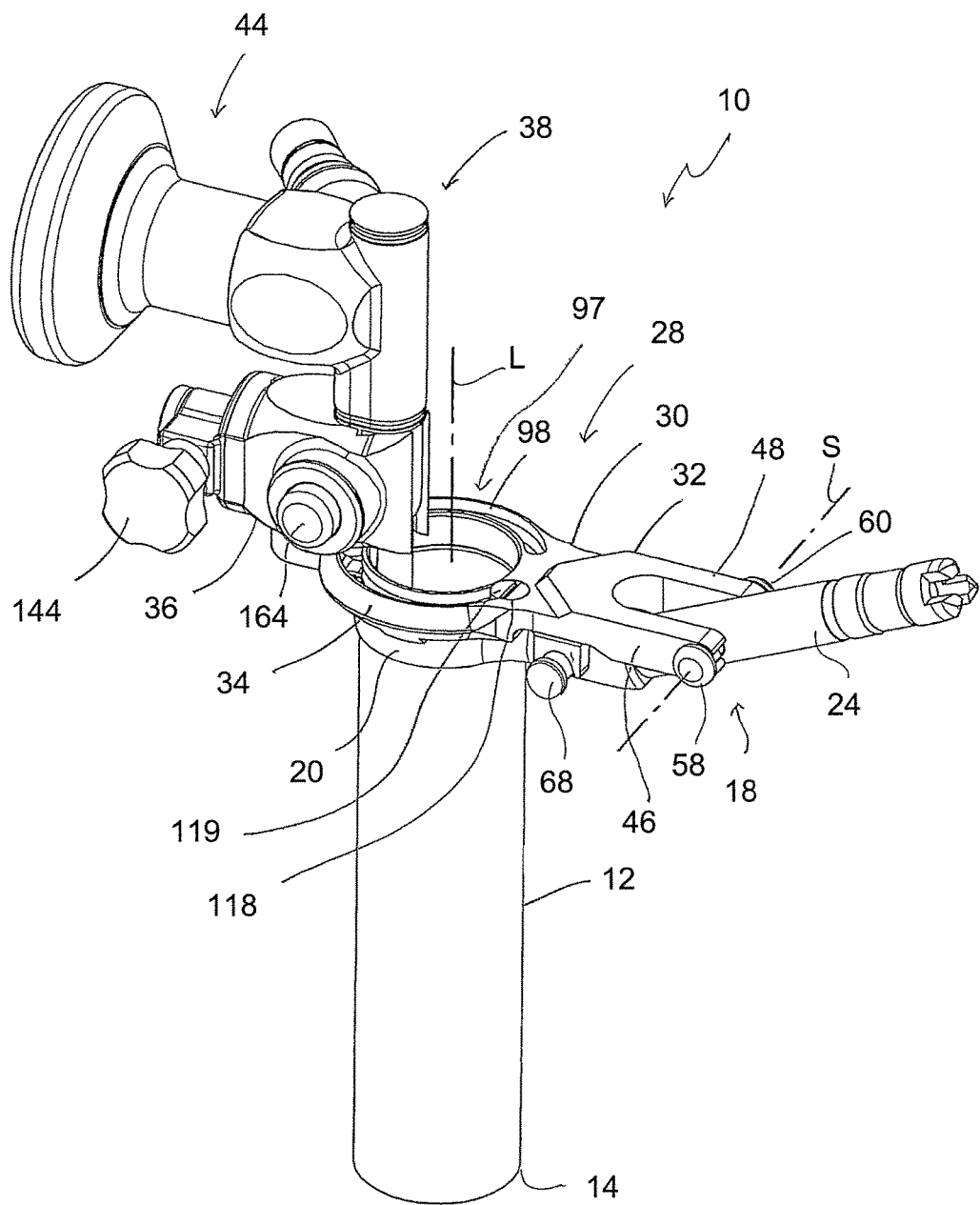
Figure 3:
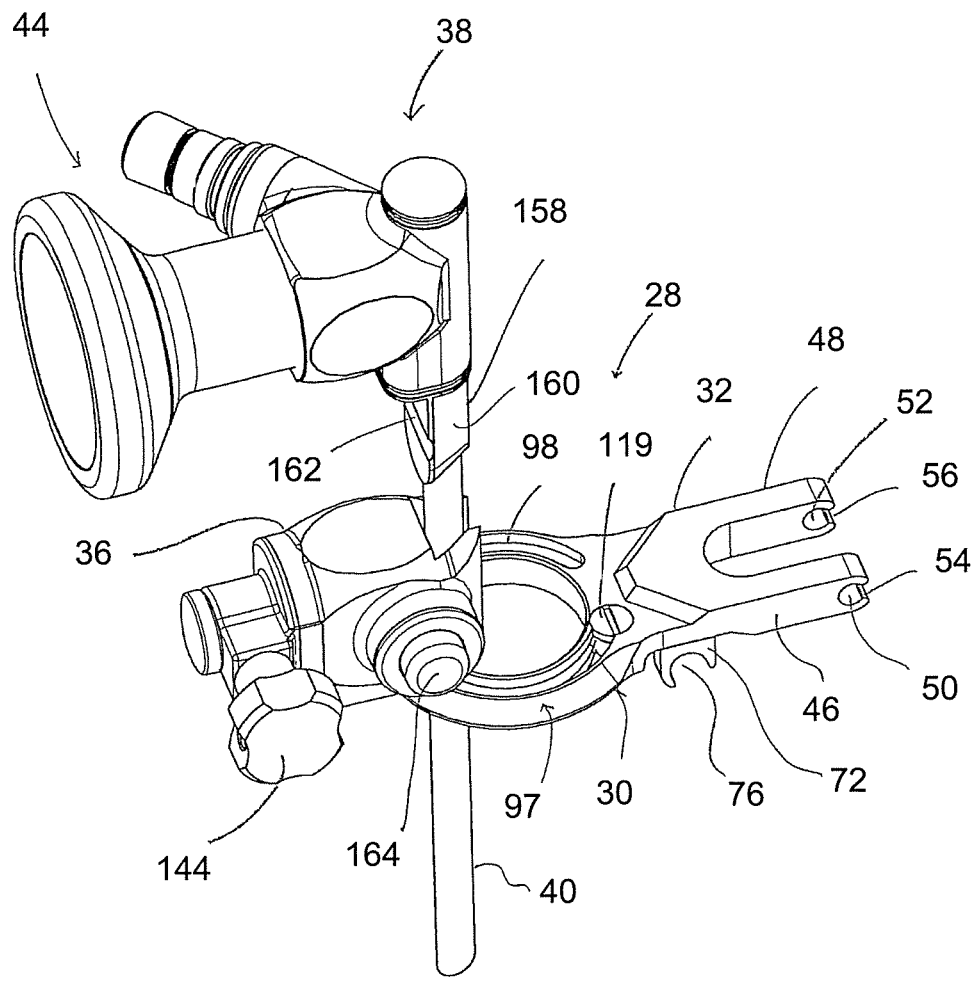
Figure 4:
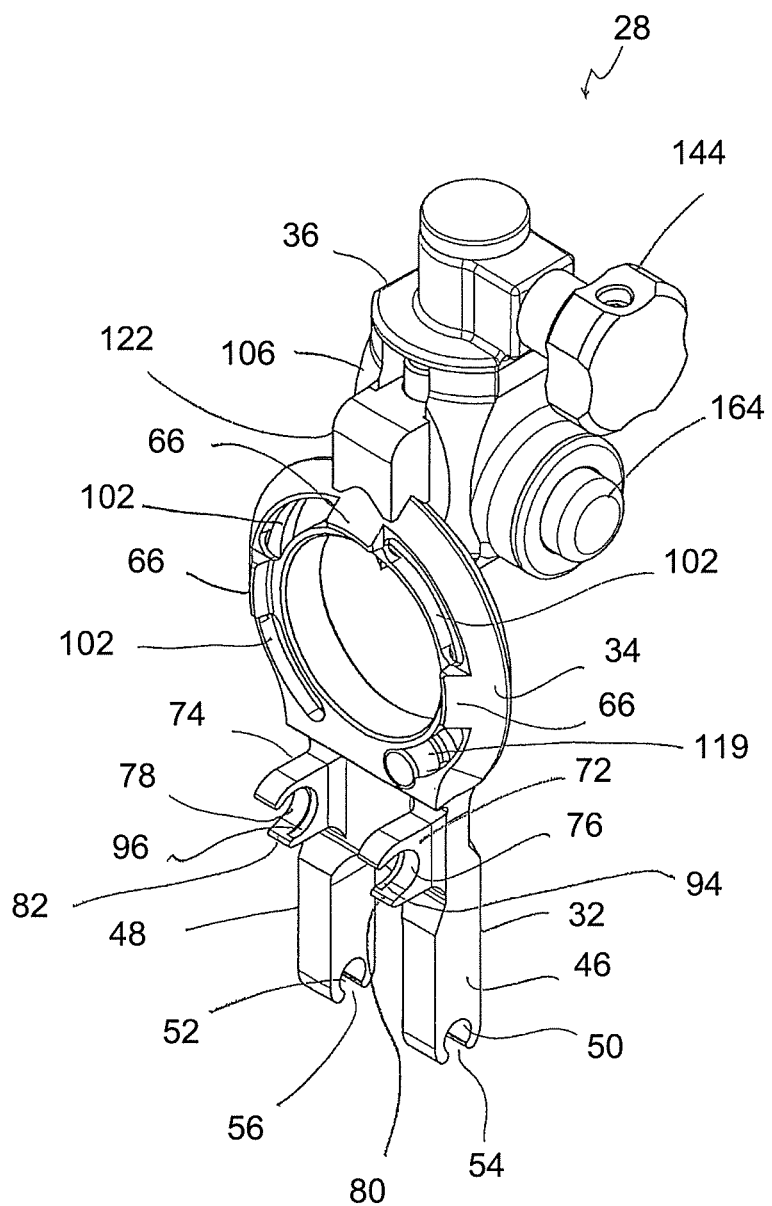
Figure 5:
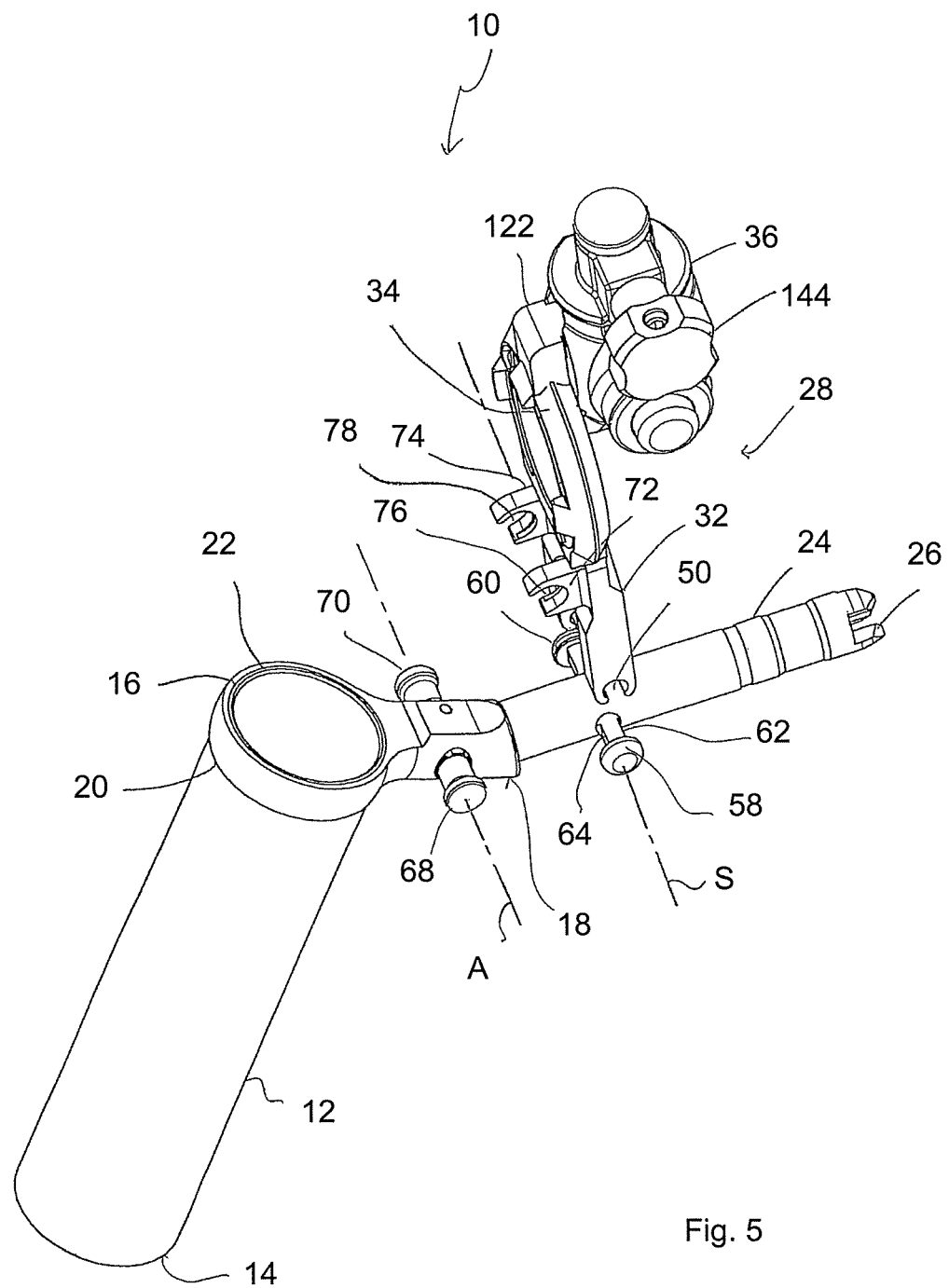
Figure 9:
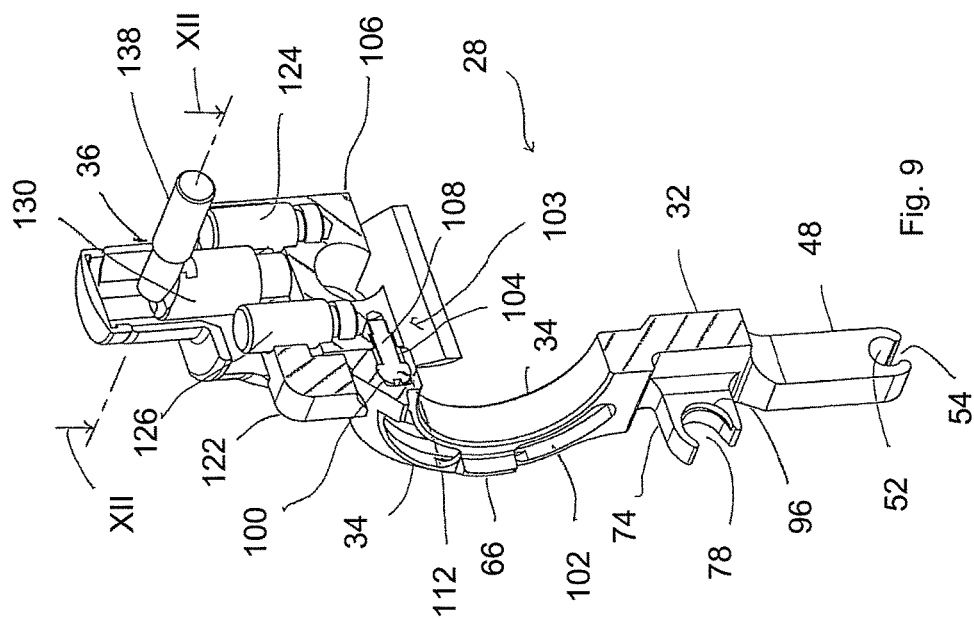
Figure 8:
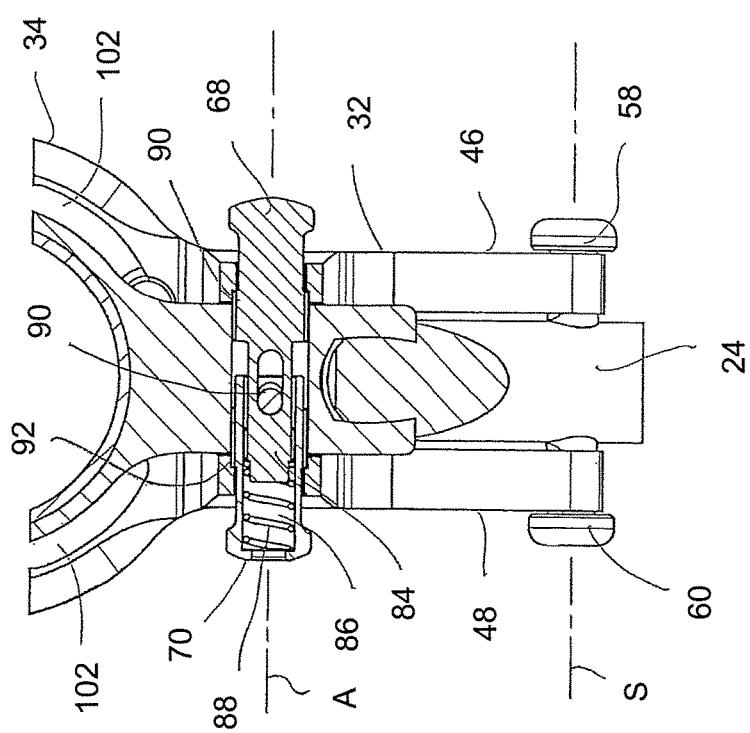
Figure 10:
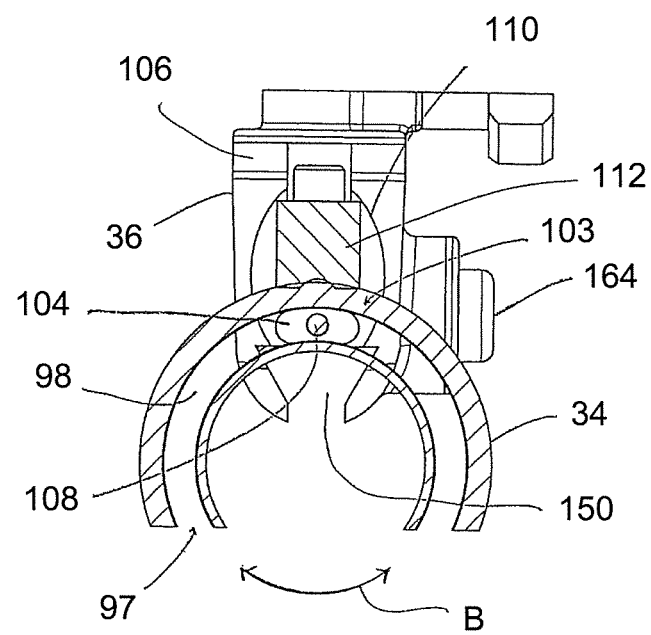
Figure 11:
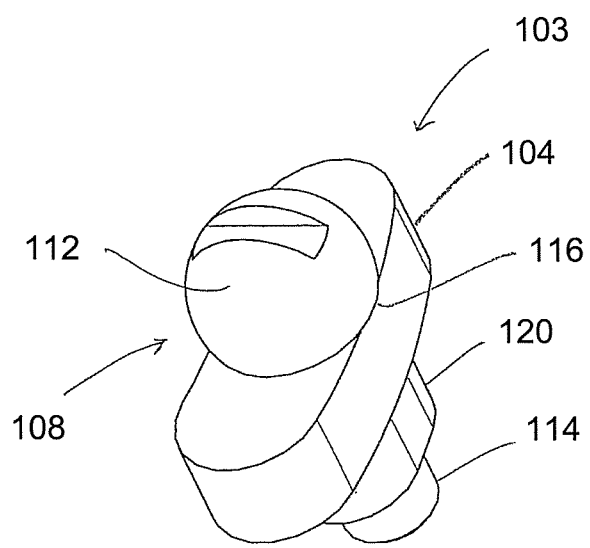
Figure 12:
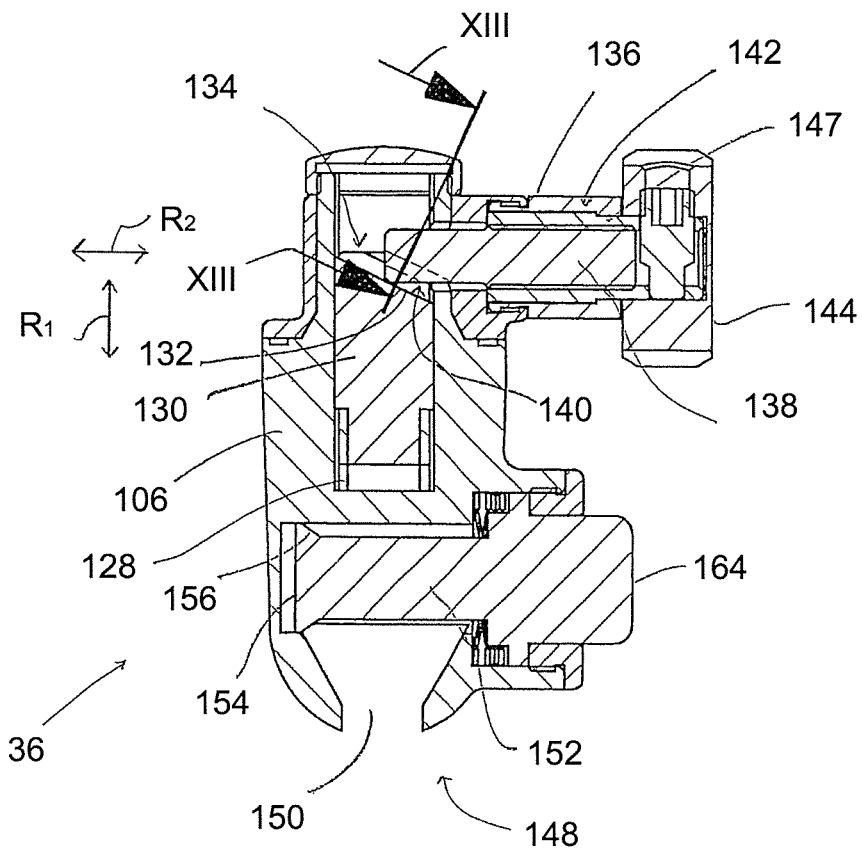
Figure 13:
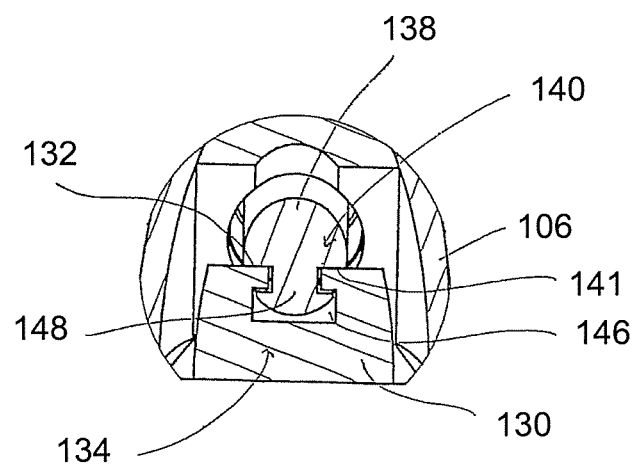
Figure 14:
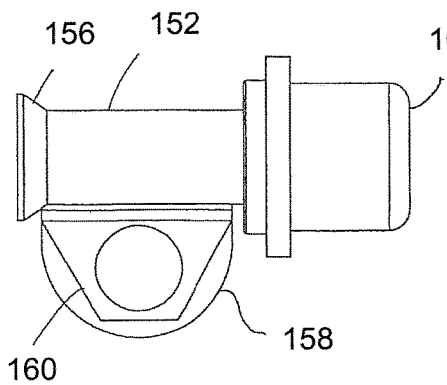
Figure 14:
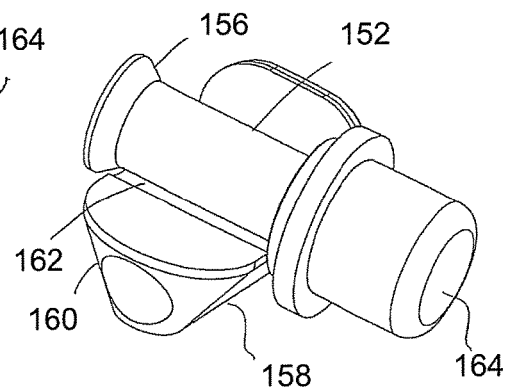
Figure 15:
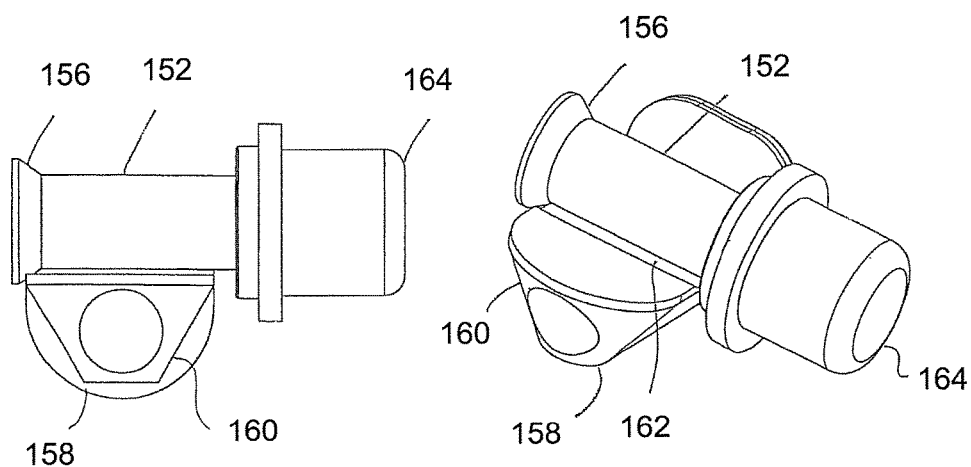
Figure 17:
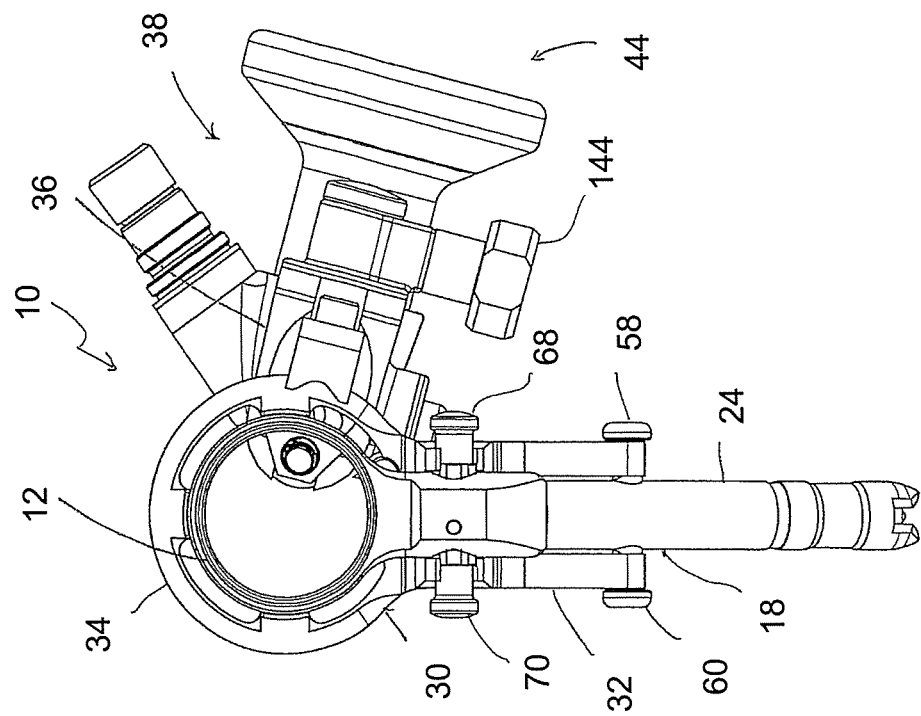
Figure 16:
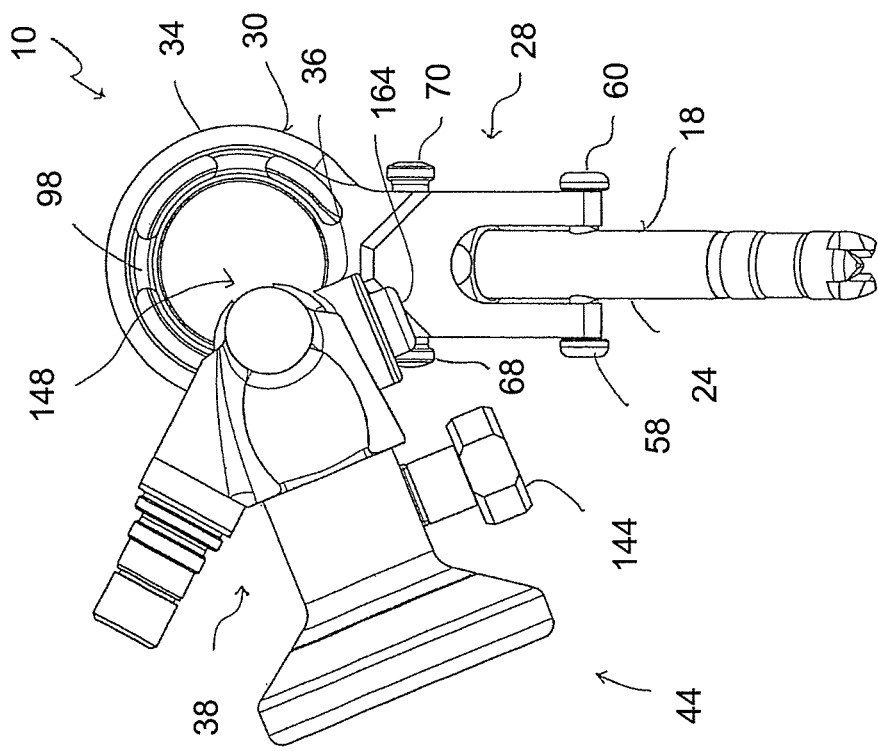
Figure 18:
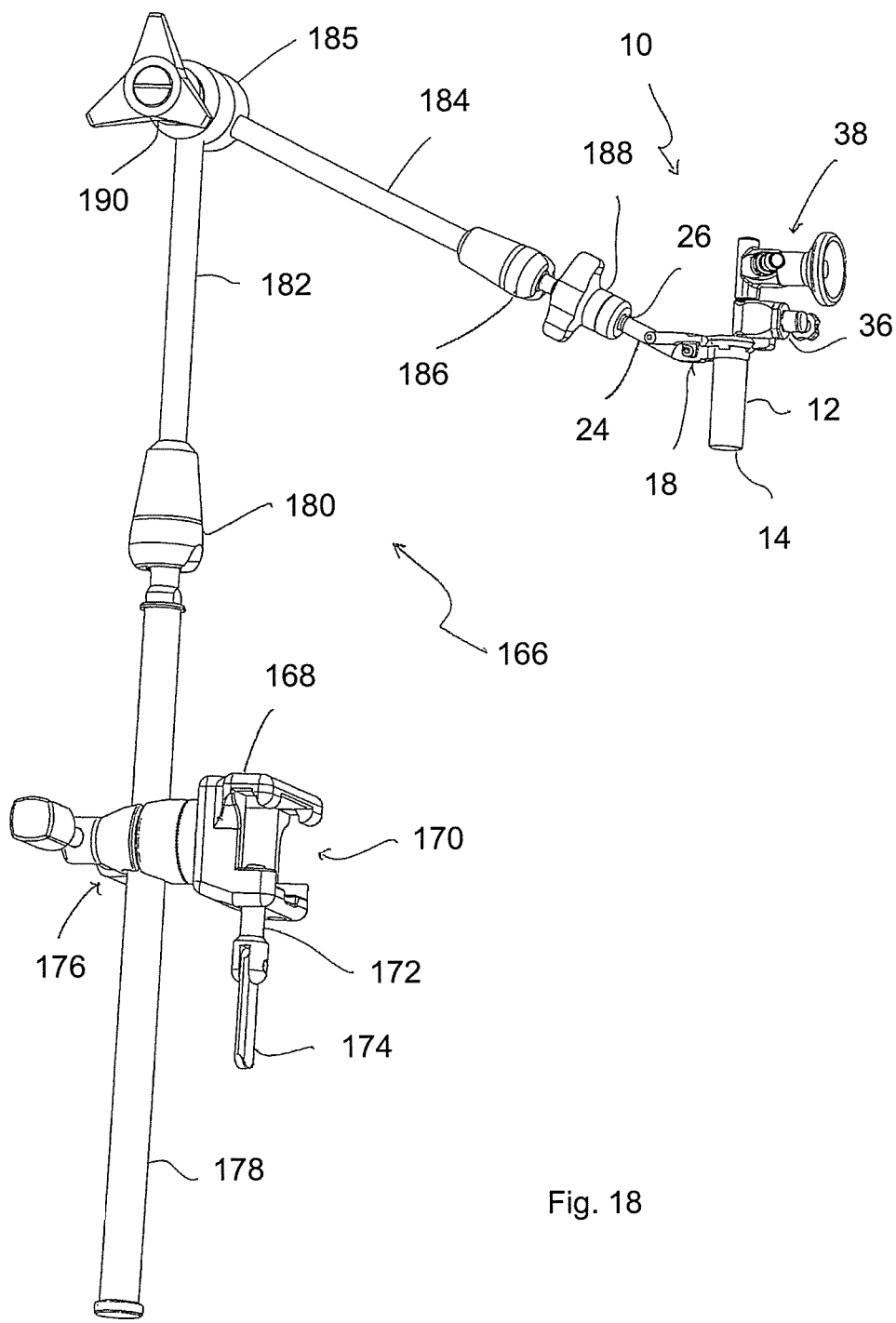
Figure 20:
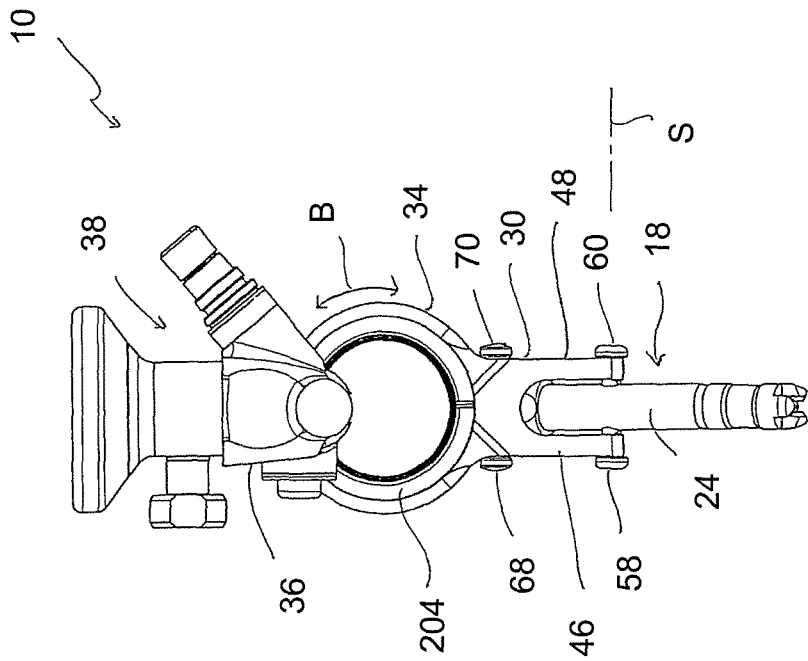
Figure 19:
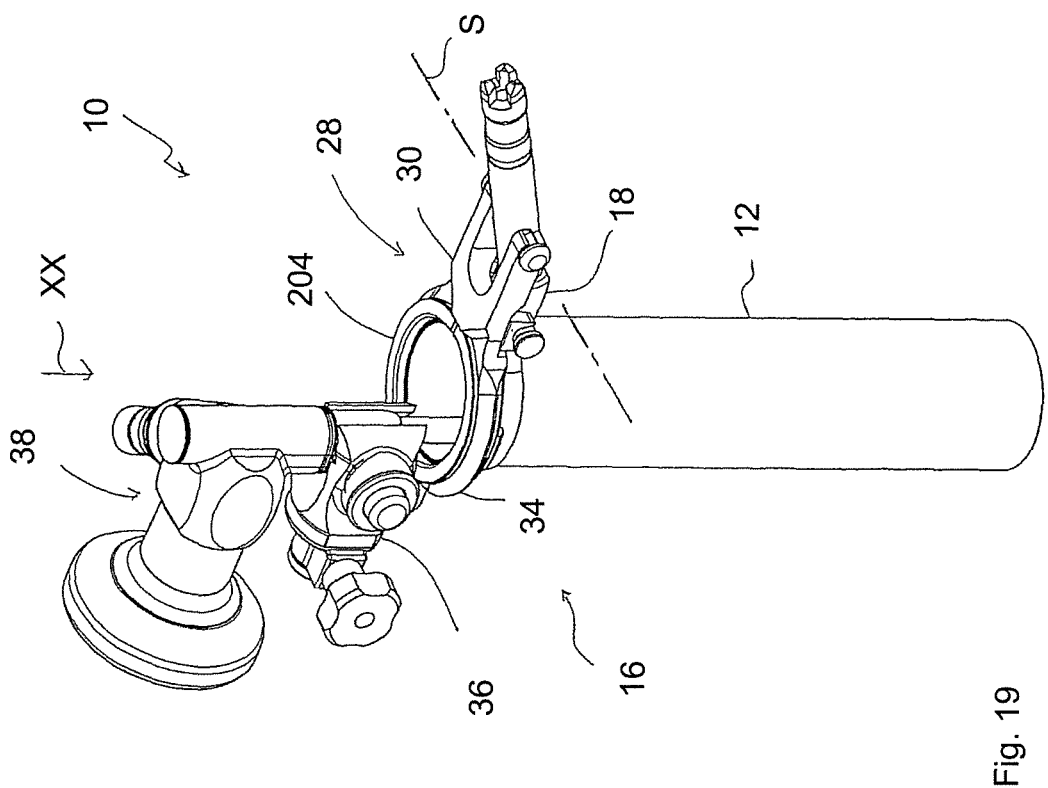
Figure 22:
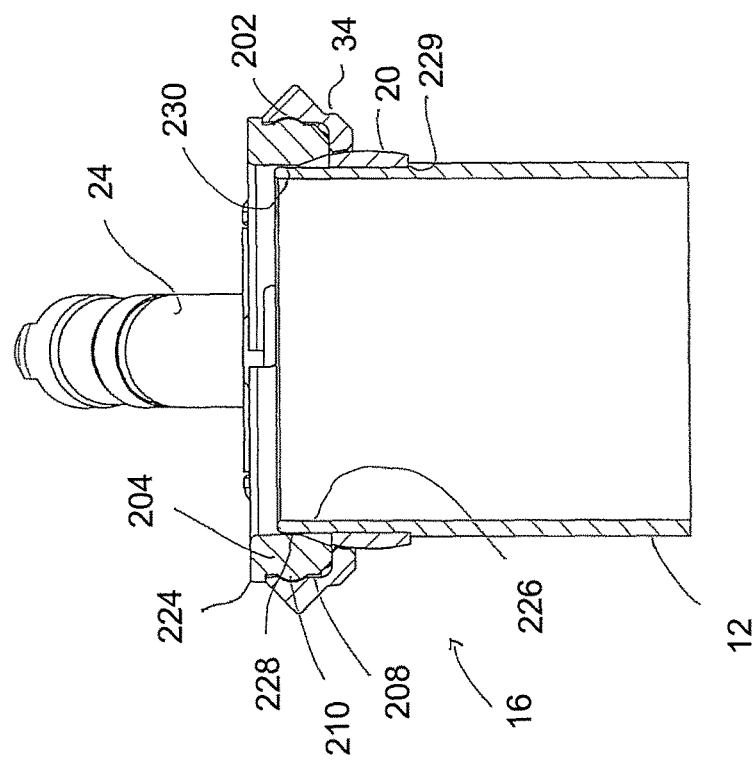
Figure 21:
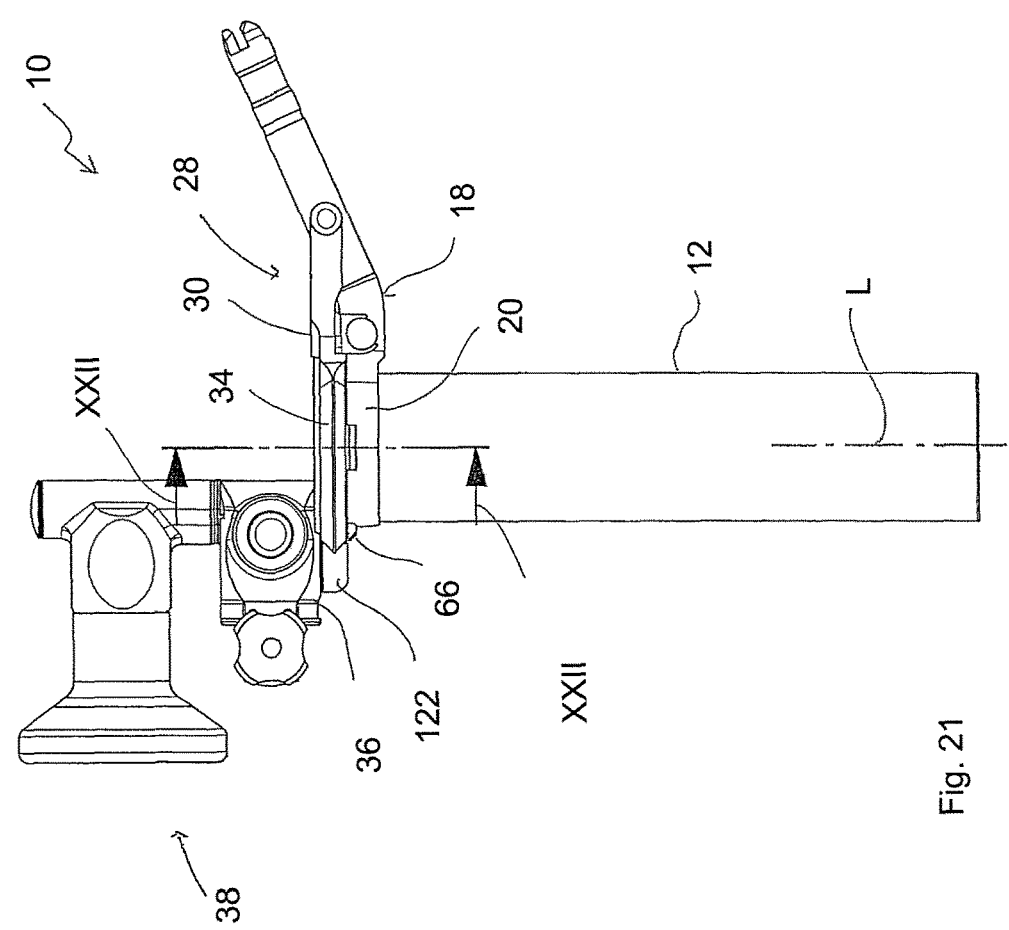
Figure 23:
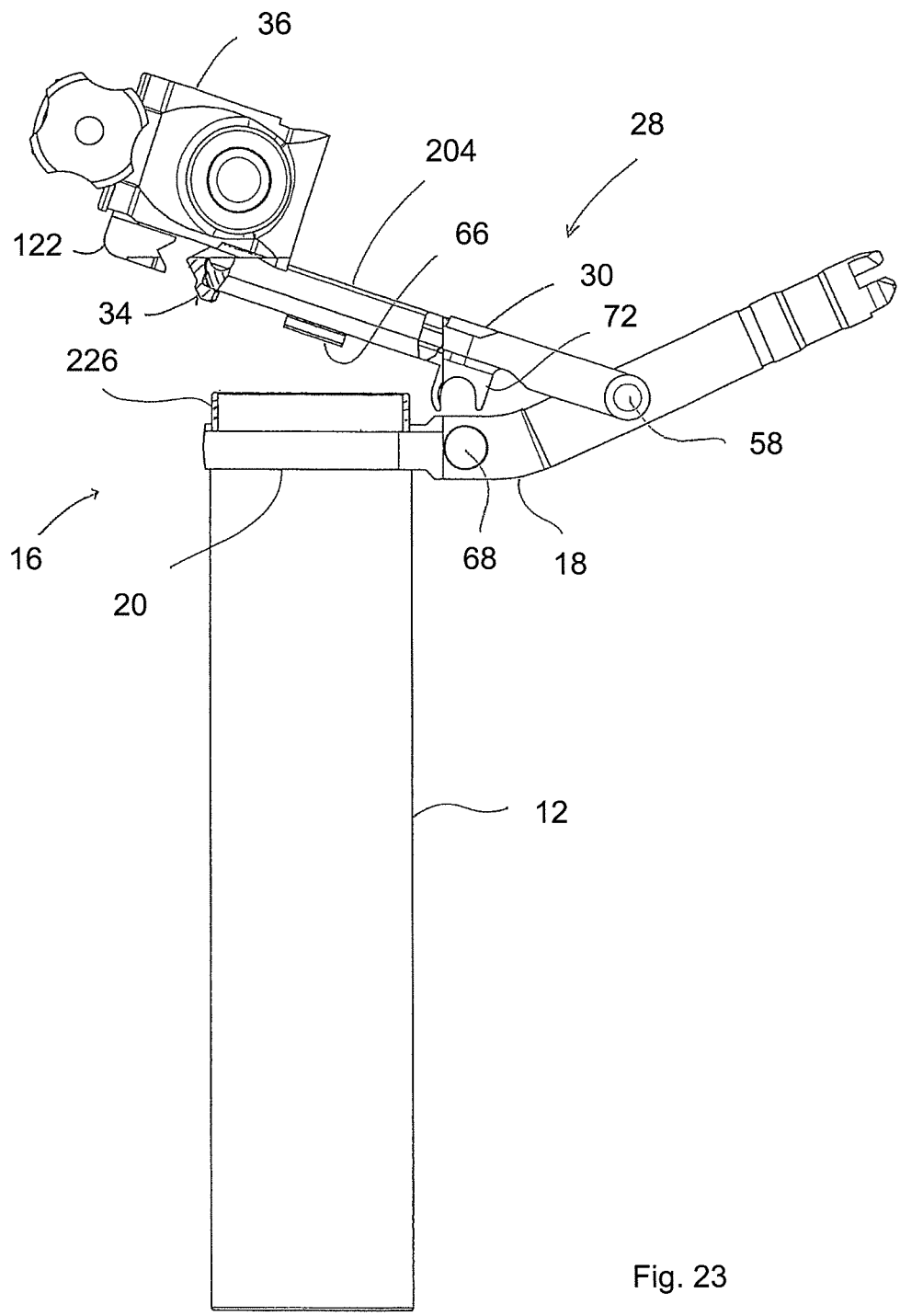
Figure 24:
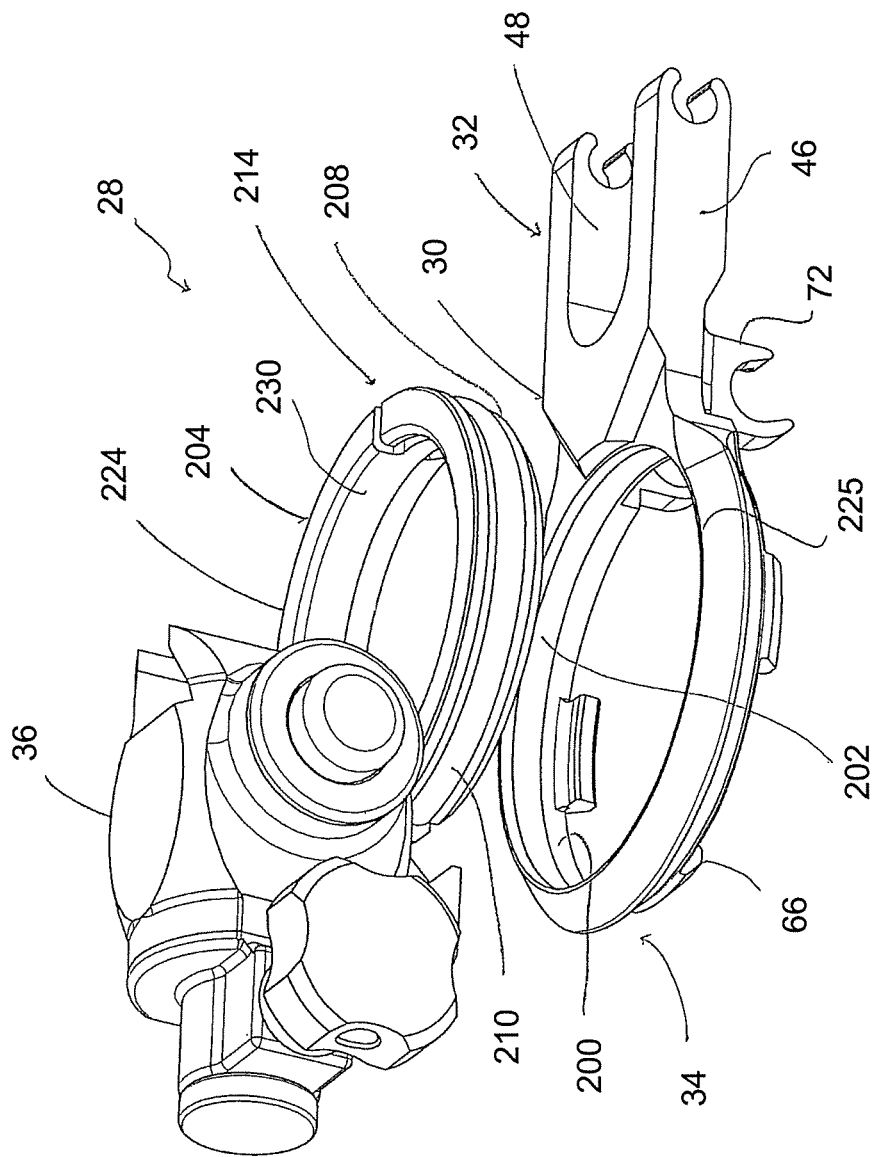
Figure 25:
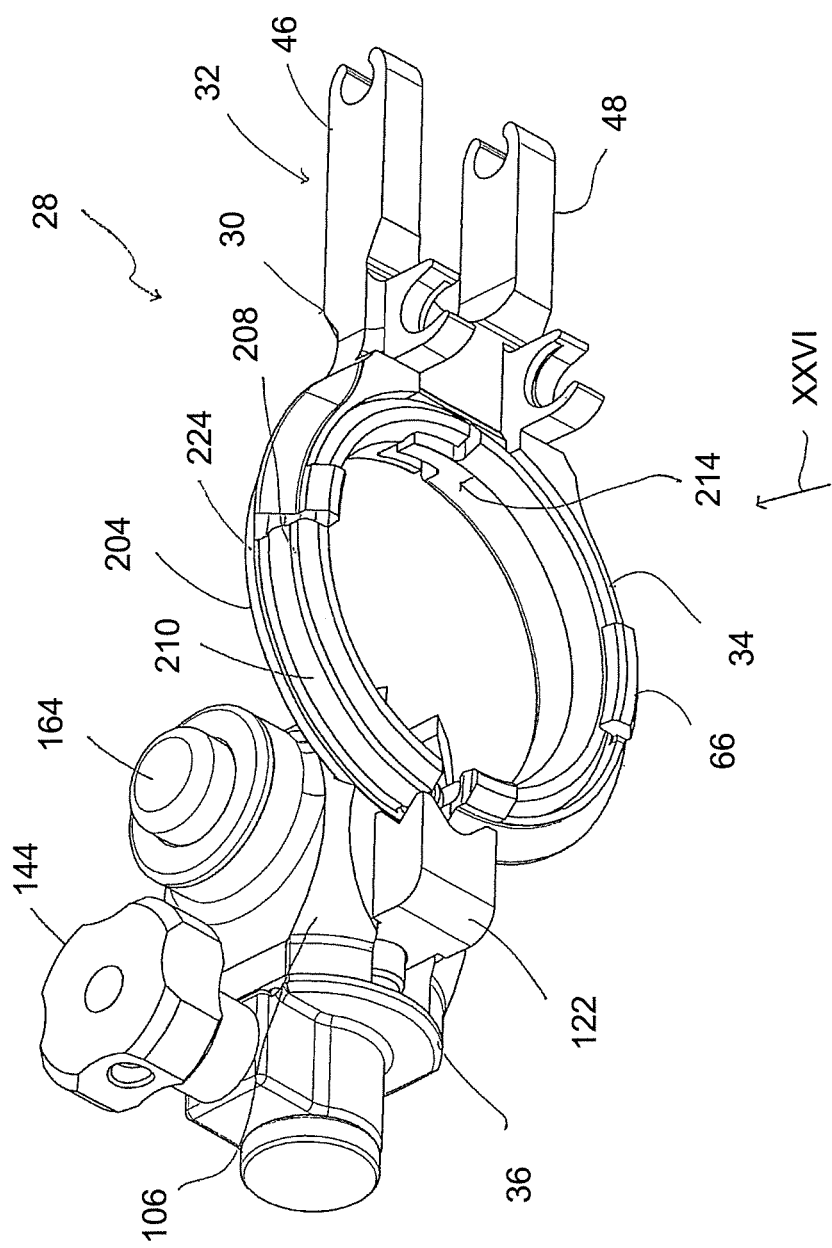
Figure 26:
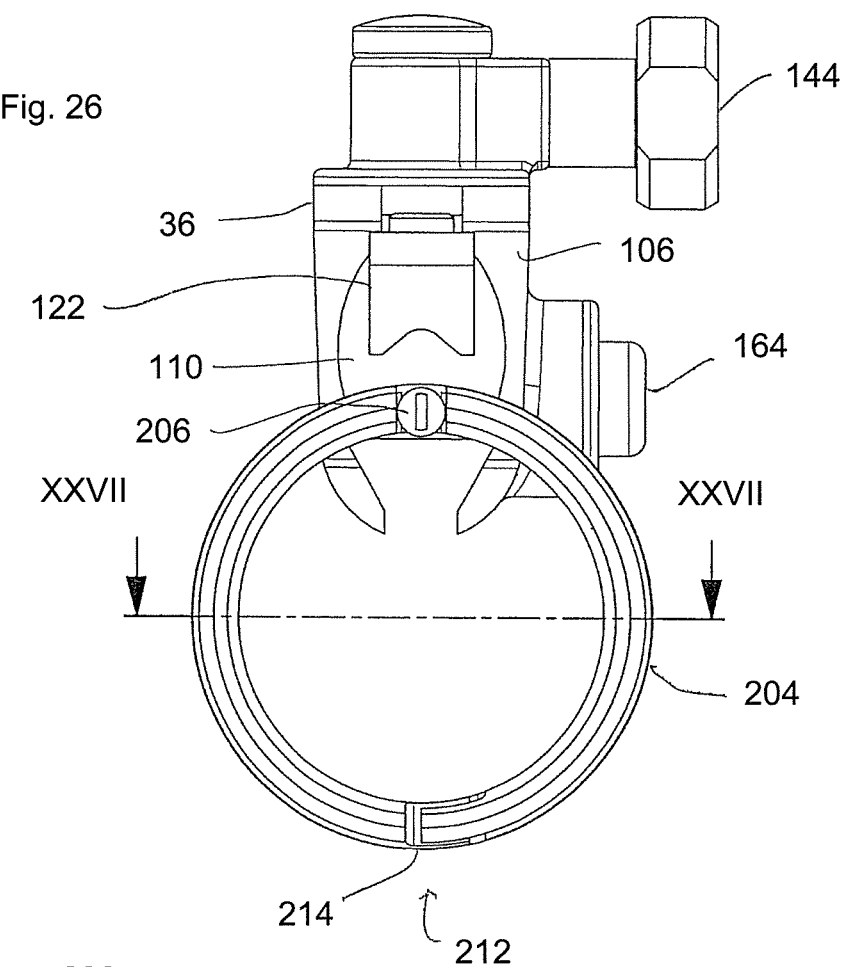
Figure 27:
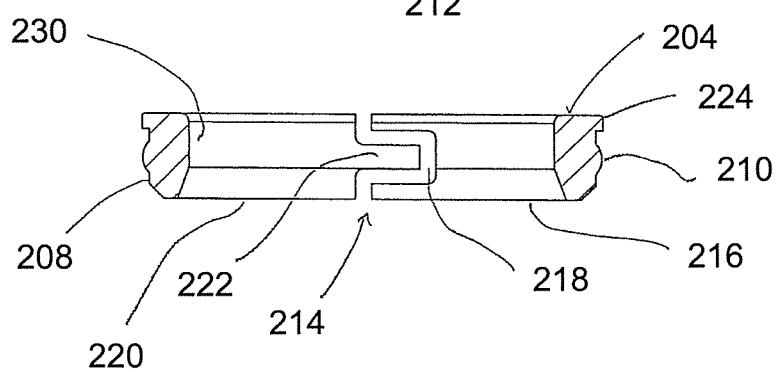
Figure 28:
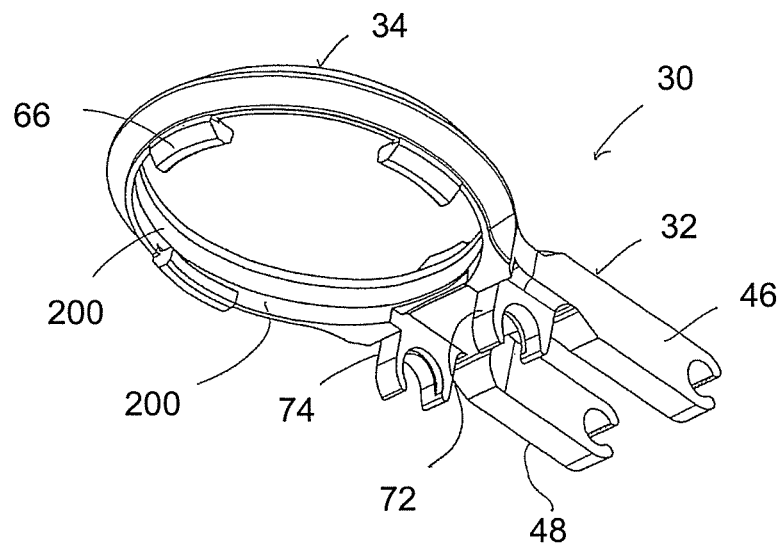
Figure 29:
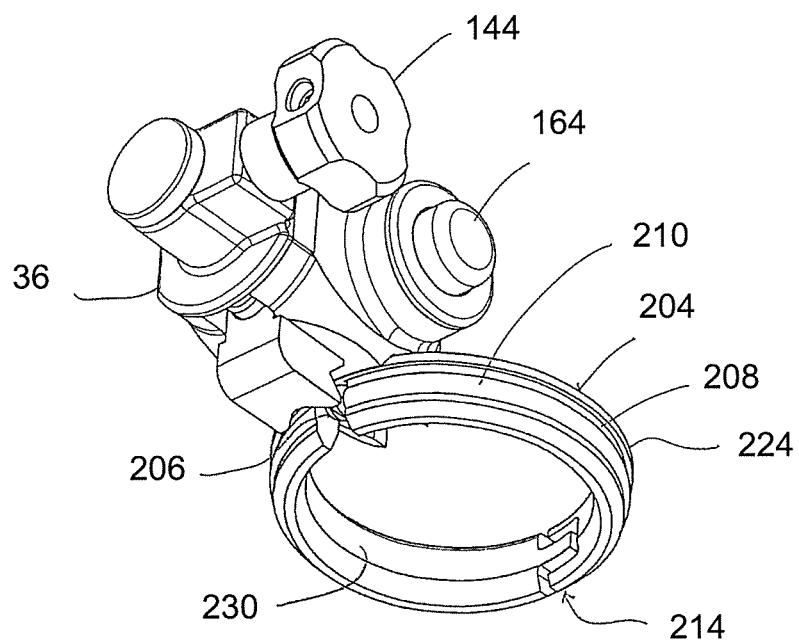

The present invention will be described in detail below with reference to the attached figures. The following is shown:

FIG. 1 A side view of a device for providing an access opening in a body, with an optics system carried thereon;

FIG. 2 A perspective view of the device in FIG. 1 with the optics system carried thereon;

FIG. 3 In perspective view, an optics carrier arrangement of the device in FIG. 1 with the optics system carried thereon;

FIG. 4 A perspective view of the optics carrier arrangement;

FIG. 5 The device in FIG. 1 with a swivel/lock region of the optics carrier arrangement in an insertion-relative position with respect to one another in relation to a swivel bracket element;

FIG. 6 A side view of the device in FIG. 1 with the swivel/lock regions and the swivel bracket element positioned in the insertion-relative position in relation to one other;

FIG. 7 A view corresponding to that in FIG. 6 with an optics carrier arrangement positioned in an operating position connecting to a proximal end of the device body;

FIG. 8 A partial sectional view of the optics carrier arrangement, cut along line VII-VIII in FIG. 7;

FIG. 9 An additional sectional view of the optics carrier arrangement cut in one of the drawing planes of the sectional planes corresponding to FIG. 7;

FIG. 10 An additional partial sectional view of the optics carrier arrangement cut longitudinally along a line parallel to line VII-VIII;

FIG. 11 An enlarged image of a guide projection with an undercut engagement region;

FIG. 12 A sectional view of an optics carrier of the optics carrier arrangement, cut along line XII-XII in FIG. 9;

FIG. 13 Enlarged and shown in a sectional view, a detail of the optics carrier, cut along line XII-XIII in FIG. 12;

FIG. 14 in its views a) and b), an optics system fixing component in release position relative to an opposing fixing element;

FIG. 15 In its views a) and b), the optics system fixing element in its fixing position relative to the opposing fixing element;

FIG. 16 The device in FIG. 1 in viewing direction XIV in FIG. 1 where there is a different relative position of the optics carrier relative to the device body;

FIG. 17 The device in FIG. 1 in viewing direction XV in FIG. 1 where the optics carrier is positioned in the relative position in FIG. 14;

FIG. 18 The device in FIG. 1 carried on an adjustable stand;

FIG. 19 A perspective view of an alternative design of a device for providing an access opening in a body with the optics system carried thereon;

FIG. 20 A view of the device in FIG. 19 in the viewing direction XX in FIG. 19;

FIG. 21 A side view of the device in FIG. 19;

FIG. 22 A partial sectional view of the device in FIG. 19, cut along line) XXII-XXII in FIG. 21;

FIG. 23 A further side view of the device in FIG. 19 with swiveled optics carrier arrangement;

FIG. 24 The optics carrier arrangement of the device in FIG. 19 in an exploded view;

FIG. 25 A perspective view of the optics carrier arrangement in FIG. 19 shown partially cut;

FIG. 26 An axial view of the optics carrier arrangement in FIG. 19 in viewing direction XXVI-XXVI in FIG. 25;

FIG. 27 A sectional view of a guide ring of the optics carrier arrangement, cut along line XXVII-XXVII in FIG. 26;

FIG. 28 A guideway element of the optics carrier arrangement in perspective view;

FIG. 29 An optics carrier of the optics carrier arrangement with a guide ring provided thereon.

FIGS. 1 and 2 show a device 10 for providing an access opening in a body during performance of a percutaneous surgical intervention on a spinal column, for example in the region of the lumbar vertebrae or in the region of the cervical vertebrae. The device 10 comprises a device body 12 with a tubular shape and extending along a longitudinal axis L, which is also generally referred to as a trocar. The device body 12 thereby advantageously has a cylindrical and circular shape. During the performance of a surgical intervention, the device body 12 is positioned with a distal end 14 in a body that is to be treated, for example a human body. A proximal end 16 lies outside the body being treated, but comparatively close to the skin or surface of the body.

On the device body 12 close to the proximal end 16, a swivel bracket element generally designated as 18 is provided. This is comprised of a fastening region 20, which advantageously circularly encloses the device body 12 and is permanently materially bonded to it, for example by welding or gluing. As can be recognized particularly in FIG. 5, the fastening region 20 is positioned in relation to the device body 12 such that it substantially ends flush with the proximal end 16 in the direction of the longitudinal axis L of the device body, or with the abutting face 22 of the device body 12. In that way, the swivel bracket element 18 is positioned as closely as possible to the proximal end 16 of the device body 12. Thus only the longitudinal section of the device body 12 that is covered by the fastening region 20 cannot be introduced into the body that is to be treated. As can be seen in the figures, this longitudinal section is relatively short, however. In this way, all the system regions explained below move very close to the surface of the body to be treated.

The swivel bracket element 18 also includes a carrier region 24 that extends in part at an angle to the fastening region 20. This carrier region 24 at its free end 26 lying at a distance from the device body 12 can be designed for fixed coupling with an adjustable stand, so that the entire device 10 can be held steady during execution of a surgical intervention. In addition, in the carrier region 24 an optics carrier arrangement 28 can be pivoted about a swivel axis S that is orthogonal to the drawing plane.

The optics carrier arrangement 28 comprises a guideway element 30 with a swivel/lock region 32 that is to be coupled in pivotable fashion with the carrier region 24 of the swivel bracket element 18 and with a guideway region 34 which, in the operating position of the guideway element 30 recognizable in FIGS. 1 and 2, is positioned so as to be attached or axially adjacent to the proximal end 16 of the device body 12.

An optics carrier 36 is carried on the guideway region 34 such that the carrier is, on the one hand, movable along a path of motion B (see FIG. 10) that circularly encloses the longitudinal axis L of the device body (see FIG. 10), but which can be fixed in any position along this path of motion B relative to the guideway region 34.

An optics system generally designated as 38 can be fixed on the optics carrier 36 when the guideway element 30 is positioned in its operating position. The optics system 38 is comprised of a rod-like optics region 40 that extends along the interior surface of the device body 12, the optics region thus running eccentrically with respect to the longitudinal axis L of the device body and having, for example in the interior of the device body 12 but lying near the distal end 14, an optics opening 42. This optics opening 42, or the optic elements provided in the optics region 40, define a field of view F through the distal end 14 of the device body 12, said field of view being variable by moving the optics carrier 36, and thus the optics system 38, along the path of motion B, in order to optically discern, in comprehensive manner, the area to be treated during a surgical intervention.

The optics system 38 also comprises an imaging region 44 in which, for example by visual observation with the eye, but likewise also by means of electronic image capture, the region of the body being treated observed through the field of view F is discernable, or can be depicted, or a connection to a monitor screen can be established.

The optics carrier arrangement 28 shown in FIG. 4 is designed in a fork shape in the swivel/lock region 32 of the guideway element 30, having two forked end regions 46, 48 which advantageously extend substantially parallel to each other. In each of these forked end regions 46, 48, a swivel recess 50, 52 with, for example, a substantially circular profile is provided. In a surrounding region of these circular profiles, for example, an opening is formed in each forked end region 46, 48 so that each swivel recess 50, 52 in this surrounding region is open, for example in the direction of a longitudinal extension of the forked end region 46, 48.

On the carrier region 24 of the swivel carrier element 18, two swivel lugs 58, 60, for example with a mushroom shape are provided, which are substantially parallel to each other and define a common swivel axis. These swivel lugs 58, 60 are sized and positioned in such a way on the carrier region 24 that when there is insertion-relative positioning of the guideway element 30 relative to the swivel bracket element 18, they can be inserted in their assigned swivel recess 50, 52. For this purpose, the guide lugs 58, 60 are flattened in two diametrically opposite regions 62, 64, while they otherwise have a substantially circular exterior circumferential contour that can be adapted to the circular interior contour of the swivel recesses 50, 52. Thus with the two flattened regions 62, 64 that lie diametrically opposite to one other, a surrounding region of a specific swivel lug is formed, which region has a smaller cross-sectional dimension, i.e. a smaller diameter, than in a surrounding region lying offset by to it by 90°, for example. In the insertion-relative positioning recognizable in FIGS. 5 and 6, this surrounding region with a smaller cross-sectional dimension is positioned such that the swivel lugs 58, 60 can be passed through the openings 54, 56 into the forked end regions 46, 58. FIG. 5 thus shows the status before sliding of the forked end regions 46, 48 onto the swivel lugs 58, 60, while FIG. 6 shows the status when the swivel lugs 58, 60 have already been received in the swivel recesses 58, 60, but before the guideway element 30 and swivel bracket element 18 are swiveled in relation to each other.

Starting from the insertion-relative position shown in FIG. 6, the guideway element 30 in the view in FIG. 6 can be pivoted about the swivel axis S in a counterclockwise direction, so that the guideway region 34 approaches the proximal end 16 of the device body 12. In the operating position of the guideway element 30 shown in FIG. 7, the guideway region 34 abuts against the proximal end 16 or the abutting face 22 of the device body 12 or/and the circular fastening region 20 of the swivel bracket element 18. Because even after a slight shift of the guideway element 30 away from the insertion-relative position shown in FIG. 6, the flattened regions 62, 64 of the swivel lugs 58, 60 are no longer aligned with the openings 54, 56 of the swivel recesses 50, 52, an unintended release of the guideway element 30 from the swivel bracket element 18 cannot take place, even during swivel movement in the direction of the operating position. Furthermore, because the swivel lugs 58, 60 with their regions of greater circumferential dimension, i.e. greater diameter, are adapted to the swivel recesses 50, 52, a relative movement of the guideway element 30 with respect to the swivel bracket element 18, regardless of the swivel movement, which is of course possible, is limited to an extent defined by unavoidable play between the fork end regions 46, 48 and the swivel lugs 58, 60. As a result, in operating position the guideway region 34 will assume an exact position relative to the device body 12. This can also be additionally supported by providing positioning projections 66 on the guideway region 34 on a number of surrounding regions or in the circular design, positioning projections, which in operating position overlap radially outward relative to the longitudinal axis L of the device body 12 in the region of its proximal end 16, or the fastening region 20 of the swivel bracket element 18 which in this region circularly encloses the device body 12 and thus additionally prevents a relative movement of the guideway element 30 with respect to the device body 12. It should be pointed out that even though in operating position these positioning projections 66 axially overlap the device body 12 to a slight degree, for purposes of the present invention the guideway element 30, in particular with its guideway region 34, is positioned to axially abut the proximal end of the device body 12, thus in the region of this proximal end 16. An overlap of this kind, in particular over the axial extent of the fastening region 20 or generally of the axial length region of the device body 12 required to secure the swivel bracket element 18 on the device body 12, nevertheless means that for purposes of the present invention, the guideway element 34 is positioned to be flush, i.e. to be axially adjacent to the proximal end 16 of the device body 12. Even an overlap of the device body 12 in the direction of the longitudinal axis L of the device body that goes slightly beyond the axial region required for fastening the swivel bracket element 18 does not preclude this.

In order to lock the guideway element 30 in the operating position, two for example substantially mushroom-shaped locking lugs 68, 70 are provided on the swivel bracket element 18, said projections substantially opposite the carrier region 24 of the swivel bracket element but extending along a common longitudinal projection axis A. Assigned to each locking lug 68, 70 there is, on the swivel/lock region 32 of the guideway element 30, a locking recess projection 72, 74 that extends, for example substantially orthogonally away from the swivel/lock region 32. In each locking recess projection 72, 74 a locking recess 76, 78 is formed, for example with a substantially circular profile. In their end regions that are oriented away from the swivel/lock region 32, the locking recess projections 72, 74 have openings 80, 82 so that the locking recesses 76, 78 are open in a surrounding region that corresponds to a specific opening 80, 82.

FIG. 8 shows that the locking lugs 68, 70 are carried on the swivel/lock region 32 and can be pushed in the direction of the longitudinal axis A of the projection. For this purpose, the locking lug 68 is design with an engaging end 84, whereas the locking lug 70 is designed with an engaging opening in which the engaging end 84 is positioned. By means of a pre-loading device 88 designed for example as a compression spring, the two locking lugs 68, 70 are pretensioned in opposite directions, and thus in the direction of a locking position. By means of a slot/bolt arrangement 90, the extent of the displacement of the two locking lugs 68, 70 in opposite directions, as well as for example toward one other, is limited.

On each locking lug 68, 70, a locking section 90 or 92 is formed by means of a gradual widening of the cross-sectional dimension of the locking lug. Assigned to these, at each locking recess projection 72, 74 a counter locking section 94, 96 is provided; said counter locking sections can be formed, for example, by means of gradual widening of the interior cross-sectional dimension of the locking recesses 76, 78 on their sides facing each other.

In order to establish the locked state during swivel movement of the guideway element 30 in the direction of its operating position, the two locking lugs 68, 70 can be loaded in the direction toward one other by means of impingement with the thumb and index finger, for example, so that they are brought closer to one other proceeding from the locked position discernible in FIG. 8. During the swivel movement, the locking recess projections 72, 74 with their openings 80, 82 assume a position in which they are aligned with the regions of smaller cross-sectional dimension of the locking lugs 68, 70 so that the latter can enter the locking recesses 76, 78 substantially without hindrance. For this purpose, it can also be provided that through the provision of the corresponding deflector bevels on the locking recess projections 72, 74, the locking lugs 68, 70 can be pressed against each other and against the preloading action of the preloading device 88, so that the locking recess projections 72, 74 can be pushed over the regions of smaller cross-sectional dimension of the locking lugs 68, 70. If the guideway element 30 is in its operating position, the locking lugs 68, 70 are inserted into the locking recesses 76, 78 to the maximum extent. If the impingement action of the locking lugs 68, 70 lapses, the latter, following the preloading action of the preloading device 88, can return to their locking position, in which the locking sections 90, 92 enter the counter locking sections 94, 96, so that it is no longer possible for the locking lugs 68, 70 to move out of the locking recesses 76, 78. Only by pressing the locking lugs 68, 70 toward one another and moving the locking sections 90, 92 out the counter locking sections 94, 96 of the locking recesses 76, 78 can the locking interaction be suspended and the guideway element 30 swiveled out of its operating position, for example in the direction of the insertion-relative position.

As can be clearly seen in FIGS. 1, 6, and 7, the swivel lugs 58, 60 on the one hand, and the locking lugs 68, 70 on the other, due to the angled design of the swivel bracket 18 in its carrier region 24, lie in different axial regions with respect to one another relative to the longitudinal axis L of the device. This makes it possible, in operating position, for the guideway element 30, which is designed with a generally uncurved configuration, to be positioned substantially orthogonally with respect to the longitudinal axis L of the device body, and thus be positioned flush with its guideway region 38 and without a tilt at the proximal end 16 of the device body 12. Here of course in principle an angled position would also be possible, with the accordingly beveled design of the proximal end 16.

Corresponding to the substantially tubular configuration of the device body 12, the guideway region 34 of the guideway element 30 is designed as substantially circular. In this guideway region 34, as a first guide element 97, an open guide groove 98 is formed in the direction away from the proximal end 16 of the device body 12. Said guide groove extends across a surrounding region of almost 360° about the longitudinal axis L of the device body and is interrupted only where the guideway region 34 connects with the swivel/lock region 32.

As shown in FIG. 9, the guide groove 98, in its groove base region that lies at a distance from the axially open end of the guide groove, is formed with a groove undercut region 100 that extends along the guideway 98. Furthermore, at a number of surrounding positions, in particular in the region between the adjacent positioning projections 66 in the circumferential direction, the guideway region 34 may have slot-like openings 102, so that the guide groove 98 is axially continuously open in a number of surrounding regions.

On the optics carrier 36, as a second guide element 103, a guide projection 104 positioned to engage the guide groove 98 is provided. Said guide projection 104, an enlarged image of which is shown in FIG. 11, is elongated in the circumferential direction of the guide groove 98 and adapted to the circularly curved contour of the guide groove 98. The guide projection 104 is sized such that particularly in the radial direction relative to the longitudinal axis L of the device body, it is received substantially without play in the guide groove 98.

The guide projection 104 could be formed as an integral part of an optics carrier body 106 of the optics carrier 36. In the example shown, the guide projection 104 is formed as a separate component and fixed by means of a threaded bolt 108 on the side 110 of the optics carrier 106 facing the guideway region 34. To that end, the threaded bolt 108 can on the one hand overlap the guide projection 104 with its bolt head 112 and on the other can be screwed with a threaded portion 114 into a threaded opening of the optics carrier 106 and be secured against unintended release for example by means of gluing.

One can see in FIG. 11 that the bolt head 112 has a larger lateral dimension than the guide projection 104. This means that the bolt head 112 projects in a radial direction beyond the guide projection 104 and, as shown in FIG. 9 can in this way be positioned so as to engage in the groove undercut region 100. The bolt head 112 thus forms an undercut engagement region 116, with at least one region that projects radially beyond the guide projection 104.

In order to mount the optics carrier 34 on the guideway element 30, the approach can be that first the bolt 108 with its bolt head 112 is passed through an assembly opening 118 that is enlarged relative to the radial extent of the guide groove 98, said assembly opening being formed in the guideway element 30 in an undercut region of the guide groove 98, and the bolt then being moved in the circumferential direction in the surrounding region of one of the openings 102. The assembly opening 118 is then closed by a closure element, for example a cap screw 119, so that release of the bolt 108 from the guide groove 98 is no longer possible. Then the guide projection 104 can be inserted into the guide groove 98, or introduced via the shaft of the bolt 108. In a subsequent step, the optics carrier 36 is positioned over the guide projection 104 and moved axially in the direction of same. In order to ensure a defined relative position between the optics carrier 36 and guide projection 104, an alignment projection 120 with a non-rotationally symmetrical outer circumference contour can be formed on the guide projection 104, it being possible to fit said alignment projection into a complementarily formed recess on the side 100 of the optics carrier body 106, and thus guarantee an alignment of the guide projection 104 that is secure against relative rotation in relation to the optics carrier body 106. Then a screwdriver can be passed through one of the openings 103 and act on the bolt head 112 in order to screw the threaded portion 114 of the bolt 108 into the assigned internal thread opening in the optics carrier body 106. A state is then achieved in which, due to the precise positioning of the guide projection 104 as well as of the undercut engagement region 116 in the guide groove 98, a precise position as well as guidance of the optics carrier 36 along the guide groove 98, and thus along the circular path of motion B, is enabled.

In order to fix the optics carrier 36 relative to the guideway regions 34, a fixing element 122 is provided. This radially encompasses, from the outside, the guideway region 34 relative to the longitudinal axis L of the device body. In order to achieve stable fixation, especially also in an axial direction, the guideway region 34 is designed on its exterior peripheral region with, for example, a convex V-shaped profile and is overlapped by the fixing element 122 with a correspondingly concave V-shaped profile. The locking component 122 is movably carried on the optics carrier body 106 in a substantially radial direction relative to the longitudinal axis L of the device body. In order to achieve defined movement control, two guide bolts 124, 126 are provided inside the optics carrier body 106, which can be made of a number of parts; said guide bolts engage the corresponding guide openings of a section 128 of the fixing element 122 that extends inside the optics carrier body. Thus the fixing element 122 is secured against tipping and can be moved in the radial direction.

Between the two guide bolts 124, 126, an impingement bolt 130 is secured to the fixing element 122. This bolt, at its end region that lies at a distance from the fixing element 122, has first an impingement region 134 that is provided with a number of wedge surfaces 132 and is thus designed in wedge shape. By means of the guide bolts 124, 126, the fixing element 122 and thus the impingement bolt 130 that is secured to it are guided to move in a first direction of displacement $R_1$ relative to the optics carrier body 106.

In a lateral extension 136 on the optics carrier 36, a rod or bolt-like impingement component 138 is guided to move in a second direction of displacement $R_2$. This second direction of displacement $R_2$ is substantially orthogonal to the first direction of displacement $R_1$. The impingement component 138 has a second impingement region 140, by means of which the impingement component 138 mutually impinges with the first impingement region 134 on the impingement bolt 130. The second impingement region 140 is substantially provided by a longitudinal end region of the impingement component 136, whereby here as well, one or a number of wedge-shaped surfaces 141 can be provided, said surfaces mutually impinging with the wedge-shaped surface 132 of the first impingement regions 134. However, in principle, in order to obtain a cam slide unit, it is sufficient to design an impingement region, here for example the first impingement region 134, with wedge-shaped configuration.

The movement of the impingement component 138 in the second direction of displacement $R_2$ is achieved by means of the spindle drive generally designated as 142. The latter comprises an actuation wheel 144 that can be rotated for example manually, the rotation of which can be converted to axial displacement of the impingement component 138 by meshed thread regions. An internal threaded sleeve 147 that is rotatably carried on the optics carrier body 106 is non-rotatably connected to the actuation wheel 144. An external thread provided on the impingement component 138 is in engagement with the internal threading of this internal threaded sleeve. Because the impingement component 138 cannot rotate about its longitudinal axis due to a positive lock between the impingement component 138 and the impingement bolt 130, upon rotation of the threaded sleeve 147, which basically is axially secured on the optics carrier body, the impingement component is forced to move in its longitudinal direction such that, depending on the orientation of this displacement, owing to the positive lock, the impingement bolt 130 is moved in one or the other orientation of the first direction of displacement $R_1$.

The impingement component 138 and the impingement bolt 130 are in a positive lock with one another in the area of the two impingement regions 134, 140. For this purpose, a groove 146 formed for example with an undercut can be provided on the impingement bolt 130, into which groove a corresponding engagement region 148 of the impingement component 138 is guided. In this way, a force can be transmitted between the two impingement regions 134, 140 $R_1$ in both orientations of the first direction of displacement, so that a displacement of the impingement component 138 to the left in the representation in FIG. 12 leads to a displacement of the impingement bolt 130 downward, and thus to movement of the fixing element 122 into its fixed position, applying force to the guideway region 34. If the impingement component 138 in the representation in FIG. 12 is moved to the right, it pulls the impingement bolt 130 upward, i.e. away from the guideway region 34. The fixing element 122 follows this movement, so that mutual fixation with the guideway region 34 is suspended, and the optics carrier 36 is released for movement along the guide groove 98.

It should be pointed out that here, in principle, an arrangement is also conceivable in which the impingement component 138 can act on the impingement bolt 130 and thus on the fixing element 122 only in the direction of the fixed position, thus in FIG. 12 can only impinge downward, whereas movement in the opposite direction of the fixing element 122 or the impingement bolt 130, takes place by means of a preloading arrangement that acts between the fixing element 122 or the impingement bolt 130 and the optics carrier body 106, for example a compression spring.

FIG. 12 also shows an optics fixation region 148 provided on an optics carrier 36. This optics fixation region includes a dovetail interior profile 150 and an optics system fixing element 152 that is displaceable on the optics carrier 36 against spring tension. In its end region, the optics system fixing element 152 has an enlarged fixation region 156 shaped like a truncated cone, said fixation region engaging the contour of the dovetail interior profile 150 when the position of the optics system fixing element 152 is as shown in FIG. 12.

Provided in the optics system 38 is an opposing fixing element 158 that can be seen in FIG. 3, said opposing fixing element being designed with a dovetail exterior profile 160 that is complementary to the dovetail interior profile 150. Assigned to the optics system fixing element 152, in the opposing fixing element 158, is a recess 162 that corresponds to the direction of extension of the optics system fixing element 152. When the dovetail exterior profile 160 is fully inserted into the dovetail interior profile 150 on the optics carrier 36, the recess 162 lies opposite the optics system fixing element 152.

FIG. 14 shows, in its representations a) and b) a state in which the optics system fixing element 152 has been pushed against its spring preload, for example by the application of pressure to an actuator button 164 that projects out of the optics carrier 36, so that the truncated-cone-shaped fixation region 156 moves out of the contour of the dovetail interior profile 150. In this state, the opposing fixing element 158 can be pushed into the dovetail interior profile 150 until a relative position between the opposing fixing element 158 and the optics system fixing element 152 that is discernable in FIGS. 14a) and 14b) is been achieved. If the impingement effect is subsequently released, the optics system fixing element 152 returns to the position shown in the FIGS. 12 and 15a) and 15b), in which the truncated-cone-shaped fixation region 156 engages the recess formed in the opposing fixing element 158. In this way, a positive-lock formed on the optics system 38 between the optics carrier 36 and the opposing fixing element 158, which prevents the opposing fixing element 158 from moving out of the dovetail interior profile 150. In order to remove the optics system, it is necessary to bring the optics system fixing element 152 by impingement into the position shown in FIGS. 14a and 14b), i.e. to disengage the fixation region 156 from the recess 162. After that, the counter fixing element 158 can be pulled out of the dovetail interior profile 150 and the optics system 38 thus released from the optics carrier.

With the optics system 38 affixed to the optics carrier 36, the optics carrier 36 can be pushed in the manner described above along the guide groove 98 on the guideway region 34 and can be brought, for example, to the position shown in FIGS. 16 and 17, or likewise in any position that is desired along the guide groove 98 or the circular path of motion B defined by it, and fixed in any desired position. During this movement, the optics region 40 likewise moves inside the device body 12 in a circular path of motion, but always near the interior surface of the device body 12, so that regardless of the particular position of the optics system 38 along the path of motion B, a comparatively large cross section, not substantially impaired by the optics system 38, remains intact for the insertion of endoscopic instruments or the like into the body to be treated.

Below the procedure will be described by which the previously described device 10 can be used when performing a surgical intervention, for example in the area of the spinal vertebrae of a human or animal body.

First, at the site where the surgical intervention is to be performed, an incision of the required size is made. By means of a dilatation system, which for example may include a number of dilatation sleeves with differing external and internal diameters relative to one other, this incision is expanded to the size required for the performance of the surgical procedure. In so doing, starting with a dilatation sleeve with a small diameter, the dilatation sleeves are successively pushed over one another, until the desired size of the opening is achieved. Through the last dilatation sleeve of the dilation system that is introduced into the incision, thereby expanding the incision, the device body 12 is introduced into the body to be treated to the desired depth. For this purpose, variously sized device bodies 12 can be held in readiness so that depending on the opening size required, only the minimum opening size needed will be selected, which in turn will also result in minimum stress to the body undergoing treatment.

After the introduction of the device body 12 into the body to be treated, the carrier region 24 can be locked onto an adjustable stand in order to ensure that during performance of the surgical procedure, no undesired movement of the device body 12 and thus of the entire device 10 will take place.

During the introduction of the device body 12 into the body to be treated, the optics carrier arrangement 28 is advantageously not on the swivel bracket element 18, which facilitates handling of the device body 12 with the permanently attached swivel bracket element 18. Because the optics carrier arrangement itself 28 is not already for on the device body 12, there is of course also no optics system 38 coupled to the device body 12.

Once the device body 12 is in the required position and advantageously firmly locked in this positioning, the optics carrier arrangement 28, comprising the guideway element 30 and the optics carrier 36, is first positioned in the insertion-relative position relative to the swivel bracket element 18, with the optics system 38 still being unconnected to it. The guideway element 30 is connected at its swivel/lock region with the carrier region 24 of the swivel bracket element 18 for swivel movement and pivoted into operating position. In so doing, it is advantageously possible, by using the locking lugs 68, 70 to produce the locking effect discussed above, so that the guideway region 34 is firmly and definitely positioned adjacent to the proximal end 16 of the device body 12, possibly slightly overlapping the device body in the region of the proximal end 16.

Subsequently the optics system 38 can be introduced in the direction of the longitudinal axis L of the device body with its opposing fixing element 158, or its dovetail exterior profile 160, into the dovetail interior profile 150 on the optics carrier body 106. During this insertion movement, the optics system fixing element 152 will be pushed into its release position, either by means of manual tensioning or by means of corresponding deflecting bevels, until the recess 162 is aligned with the optics system fixing element 152. In this state, the optics system fixing element 152 is brought into the fixed state due to pretensioning of said optics system fixing element, so that the opposing fixing element 158 is fixed on the optics carrier 36. In this state, the optics region 40 of the optics system 38 lies at least in some regions inside the device body 12.

Subsequently, the optics carrier 36 with the optics system 38 carried on it can be pushed along the path of motion B, i.e. along the guide groove 98 in the guideway region 34, so that the optics system 38 with its field of view F is positioned such that there is an optimal view of the area to be treated. Now the fixing element 122 can be brought into fixing position, in which it is pressed radially from the outside against the guideway region 34, so that the latter is clamped between the fixing element 122 and the guide projection 104 that engages in the guide groove 98. In this state, the optics carrier 36 and with it the optics system 38 is secured against movement along the guide groove 98.

FIG. 18 shows the device 10 with the optics system 38 carried on it on a carrier arrangement 166 generally termed an adjustable stand. This is comprised of a clamp component 168 that can be clamped to a first clamping region 170, for example on an operating table. For this purpose a clamping screw 172 can be activated by means of an actuation lever pivotably carried thereon.

In a second clamping region 176, a clamp rod 188 of the carrier arrangement 166 can be clamped onto the clamp component 168, whereby the clamp rod 178 can be brought into an appropriate sliding positioning relative to the clamp component 168, also in order to adjust the height of the device 10, and then clamped in a second clamp region 176.

By means of a ball joint 180, a first carrier rod 182 is secured in an articulated connection to the clamp rod 178. A second carrier rod 184 is pivotably coupled via a swivel joint 185 to the first carrier rod 182. By means of a further ball joint 186, the second carrier rod 184 is secured in an articulated connection to a holder component 188. On the holder component 188, the carrier region 24 of the swivel bracket element 18 can be held in the region of its free end 26.

By means of a clamp component provided on the swivel joint 186 and a for example manually actuated clamp component 190, after setting the desired position of the device 10, the two ball joints 180, 186 as well as the swivel joint 185 can be locked against movement so that on the one hand, in a then fixed position, the clamp rod 178 can be held substantially immobile relative to the first carrier rod 182, and on the other hand the second carrier rod 184 can be held immobile relative to the holder component 188, and in addition, the first carrier rod 182 can be held substantially immobile relative to the second carrier rod 184. In this state, the device 10, with the device body 12 that is already positioned in the incision made in the body to be treated, is stably positioned, thus enabling performance of the surgical procedure that is to be undertaken.

During performance of the surgical procedure, the optics carrier 36 with the optics system 38 carried on it can if required be brought into a different position by movement along the guide groove 98. In order to do this, the fixing element 122 is moved radially away in the direction of the guideway region 34 and the clamping effect of the guideway region 34 between the fixing element 122 and the guide projection 144 is released. After movement along the path of motion B, or in the guide groove 98, and after reaching the desired new position, the fixing element 122 can once again be pressed against the external circumference of the guideway region 34 and in that way fixed to the optics carrier 36.

After completing the surgical procedure performed through the device body 12, the optics system 38 is first removed from the optics carrier 38. In order to do so, the optics system fixing element 152 is brought by means of impingement into its release position, and the opposing fixing element 158 is pulled out of the optics carrier body 106. Once the optics system 38 has been removed, by pressing the two locking lugs 68, 70 against each other, they can be disengaged from the locking recesses 76, 78. Then the guideway element 30 can be pivoted out of its operating position into the insertion-relative position, so that the forked end regions 46, 48 of the swivel lugs 58, 60 can be withdrawn and the optics carrier arrangement 28 can be removed from the device body 12. Finally, the device body 12 is pulled out of the incision that has been made in the body to be treated, followed by the treatment that is then still required in the region of the incision, comprising for example suturing in the incision area. The various parts of the device 10, that is, the device body 12 with the swivel bracket element 18 carried fixedly on it on the one hand, and the optics carrier arrangement 28 with the guideway element 30 and the optics carrier 36 on the other hand, can now be sterilized separately from one another for the purpose of reuse. Then another surgical procedure can be performed in the manner described above using a device 10 and if required a dilatation system.

As already described above, device bodies 12 with different dimensions, that is different diameters and possibly optics carrier arrangements 28 matching these different sizes can be held in readiness in a device set, so that depending on the size of the access opening required, the respective device body 12 and the optics carrier arrangement 28 assigned to it are available for use.

Below, with reference to FIGS. 19 to 29, an alternative embodiment of the device 10 for providing an access opening in a body will be described. This embodiment corresponds to the greatest extent possible to the device 10 described above with regard to its structural design and its use in carrying out a surgical procedure. This also applies in particular to the fundamental design of the optics carrier arrangement 28 with the fork-like configuration of its guideway element 30 and its swivel interaction with the swivel bracket element 18. The optics carrier 36 as well, with respect to fixation of same on the guideway region 34 and with respect to the technical measures provided for the purpose of fixing an optics system 38 onto it, is substantially designed as described above, as is the case with the tubular design of the device body 12 and the swivel bracket element 18 attached to it. Thus with respect to the fundamental structural design and the functionality of these assemblies, reference will be made to the above representations. In the following description of the significant differences in structural design between the embodiment in FIGS. 19 to 29 and the embodiment that has been described above, components, or component groups that correspond to components, or component groups that are described above are designated with the same reference signs.

In the embodiment of the device 10 represented in FIGS. 19 to 29, the guideway region 34 of the guideway element 30 is designed as substantially circular, so that when positioning the guideway element 30 in its operating position, as is also discernable in FIG. 19, the guideway region 31 is also positioned by means of swiveling about the swivel axis S in the region of the proximal end 16 of the device body 12, or as will also be shown below, the guideway region in this region will also enclose the device body 12 radially outward in relation to the longitudinal axis L of the device body.

The guideway element 30, in its circular guideway region 34, has as a first guide element 97 a guide surface 200 that in operating position of the optics carrier arrangement 28 preferably completely circularly encloses the longitudinal axis L of the device body and is formed as an interior circumferential surface. Provided in this guide surface 200 is a guide recess 202 that extends, also advantageously circularly closed, in the direction of the circular path of motion B. The second guide element 103 comprises a guide ring 204 which, as can be clearly seen in FIG. 26 and in FIG. 29, is fixed by means of a fixing element 206, for example a screw bolt or similar, to the optics carrier body 106 on its side 110 positioned to face the guideway region 34. The guide ring 204 has an opposing guide surface 208 formed as a substantially closed circularly formed exterior circumferential surface. Formed on this opposing guide surface 208 is a bulging or knob-like guide projection 210, projecting radially outward, which extends in the direction of the circular path of motion B, the cross-sectional geometry of said guide projection being substantially complementary to the cross-sectional geometry of the guide recess 202.

One can also discern in FIGS. 24, 26, and 27 that the guide ring 204 is in principle circularly closed, but that in a surrounding region 212 it has an interruption 214. In this surrounding region 212, an open recess 218 in the circumferential direction is formed, for example in a circumferential section 216 of the guide ring 204. Formed in a circumferential section 220 opposite it is a projection 222 engaging the recess 218 that projects in the circumferential direction, so that the guide ring 204, particularly in an axial view, is formed as substantially completely circumferential. Between the two circumferential sections 216, 220, a circumferential intermediate space is formed, which makes it possible for the two circumferential sections 216, 220 to approach each other through the application of a load. The guide ring 204 is thus fundamentally formed as radially elastic, so that under radial pressure, its external dimension can be diminished. In particular, this reduction in the external dimension can take place to such a degree that in this compressed state, the guide ring 204 can be introduced into the guideway region 34 by its guide projection 210 until the guide projection 210 is aligned with the guide recess 202, thus lying opposite it. In order to specifically define this relative position, the positioning projections 66 that are provided at a plurality of circumferential positions on the guideway element 30 are for example designed such that they project radially inward in relation to the guide surface 200. Furthermore, on the guide ring 204, a radially outward projecting waist area 224 relative to the opposing guide surface is provided, it being possible for said waist area to come to rest against an end face 225 of the guideway region 34.

When the guide ring 204 is introduced to the maximum degree into the opening formed in the guideway region 34, the compression load can be released, so that the guide ring 204, due to its inherent radial elasticity, returns to its original form, i.e. expands radially. The guide projection 210 therefore enters the guide recess 202 and the opposing guide surface 208 comes at least in areas in contact with the guide surface 200.

In order to achieve this radial elasticity of the guide ring 204, the guide ring 204 is advantageously made of a material which, on the one hand, for example due to manual effects, allows a sufficiently strong deformation, but on the other hand can also return to its original form, that is, with the required compression it does not go into a plastically deformed state. Furthermore, this material must also be suitable for the performance of surgical procedures and the sterilization that is also required afterwards, for example at comparatively high temperatures. As the material for making the guide ring 204, PEEK material, for example, can be used.

In order to achieve, for the design in FIGS. 19 to 29, an even further improved guide function for the optics carrier 36 or the guide ring 204 provided on it in the region of the proximal end 16 of the device body 12, for example a cylindrical or tubular guide section 226 with an additional guide surface 228 designed as an exterior circumferential surface is provided. This guide section 226, as shown in FIG. 22, can be provided with an end section of the device body 12 in the region of the proximal end 16, i.e. as formed integrally with the device body 12. For example, the device body 12 can be designed in the region of its proximal end 16 to have gradually tapering wall thickness, so that on the one hand, the guide section 226 is formed, and on the other, a positioning stop 229 for the circularly formed fastening region 20 of the swivel bracket element 18 is formed.

On the guide ring 204, formed as an inner circumferential surface, an additional opposing guide surface 230 is provided, said opposing guide surface, when the optics carrier arrangement 28 is positioned in the operating position, radially outwardly surrounds the guide section 226 at the proximal end 16 of the device body 12, or can come into guiding contact with the guide section. Thus, in operating position, the guide ring 204 is positioned radially between the guideway region 34 or its guide surface 200 and the guide section 226 or its additional guide surface 228. As already explained above, in this position the guideway region 34 encloses the guide section 226 and thereby, with the shown integral design of same with the device body 12, encloses this device body 12 in the region of its proximal end 16. With this embodiment as well, according to the principles of the present invention, in operating position the guideway region 34 is positioned in the region of the proximal end 16, and is thus attached to the proximal end 16 of the device body 12, even though there is an axial overlap here between these two assemblies. This axial overlap is comparatively short. As FIG. 22 shows, the guideway region 34 does not for example completely overlap the device body 12, just as the guide ring 204 does not.

In order to fix the optics carrier 36 on the guideway region 34 of the guideway element 30, as explained in detail above, the fixing element 122 provided on the optics carrier 36 can be pressed from outside radially against the guideway region 34, which in this embodiment as well is designed with a V-shaped convex profile. Thereby, in the surrounding region in which the fixing element 122 is pressed from outside radially against the guideway region 34, the guide surface 200 and the opposing guide surface 208 are pressed more strongly against each other, so that ultimately, the guideway region 34 is clamped radially between the fixing element 122 provided on the optics carrier 36 and the guide ring 204 that is also provided on the optics carrier 36. In order to displace the optics carrier 36 with the optics system 38 carried on it along the path of motion B, this clamping effect can be released by radial movement of the fixing element 122 away from the guideway region 34, whereupon the guide ring 204 in the guideway region 34 is released for rotation about the longitudinal axis L of the device body, and in that way the optics carrier 36 with the optics system 38 carried on it can be positioned in any other circumferential position.

The design of the device 10 that is described above and shown in FIGS. 19 to 29 entails substantial advantages, particularly as regards the optics carrier 28. On the one hand, a substantially circularly closed guiding interaction arises between the guideway element 30, or the guideway region 34 of same and the guide ring 204 provided on the optics carrier 36. This means that even when an optics system 38 is carried on the optics carrier 36, and due to the weight load of the optics system, a tilting effect arises on the optics carrier 36, there is no tilt between the first guide element 97, i.e. the guide surface 200 provided on the guideway region 34, and the second guide element 103, i.e. the guide ring 204 with its opposing guide surface 208 provided on the optics carrier 36. This effect is achieved particularly efficiently when, as is shown in this case, the guide ring 204 is substantially completely circularly closed. However, it should in principle nevertheless be pointed out that this effect can also be achieved if the guide ring 204 is designed as a ring segment, for example, with a circumferential extension angle of more than 180°.

There is a further substantial advantage in that with the two surfaces that enter into guiding interaction, i.e. the guide surface 200 and the opposing guide surface 208, elements are provided that have no deep grooves or groove undercut regions, thus no volume regions that are difficult to access, for example in the interior of the guideway region 34. This is particularly advantageous during sterilization of the device 10 after performance of a surgical procedure, because there is no risk that interior volume regions will not be sufficiently sterilized.

The invention claimed is:

1. A device for providing an access opening in a human body, comprising:
a tubular device body that extends along a longitudinal axis, said tubular device body, having a distal end configured to be positioned inside a human body and a proximal end configured to be positioned outside of the human body;
a guideway element configured to be positioned in an operating position in the region of the proximal end of the tubular device body, said guideway element can be brought into said operating position by pivoting around a swivel axis with respect to the tubular device body, said guideway element having a guideway region providing a ring shaped path of motion around the longitudinal axis of the tubular device body when said guideway element is in the operating position;
a movable optics-carrier movably carried on the guideway element so as to be movable along the ring shaped path of motion provided by the guideway region for adjusting a position of the optics carrier with respect to the guideway region when the guideway element is in the operating position; and
wherein the guideway element has a swivel/lock region for pivotable mounting and locking of the guideway element in the operating position on a swivel bracket element that extends away from the tubular device body.

2. The device according to claim 1,
wherein the guideway region has a circular design and has a circular first guide element, wherein a second guide element for moving the optics carrier on its path of motion around the longitudinal axis of the tubular device body is guided along the circular first guide element and is fixable at any desired position along the first guide element.

3. The device according to claim 2,
wherein the circular first guide element is a guide groove or guide surface.

4. The device according to claim 2, wherein the second guide element is a guide projection or guide ring of the optics carrier.

5. The device according to claim 1,
wherein the swivel bracket element comprises a fastening region that circularly encloses the tubular device body and ends flush with the proximal end of the tubular device body and a carrier region that extends away from the fastening region.

6. The device according to claim 1,
wherein on the swivel bracket element, at least one swivel lug is provided, and on the swivel/lock region assembly of the guideway element, a swivel recess open in a surrounding region assigned to each swivel lug is provided for the insertion of the swivel lug.

7. The device according to claim 6,
wherein, the at least one swivel lug for insertion into a swivel recess in an insertion-relative position, between the swivel/lock region and the swivel bracket element, in at least one surrounding region has a smaller cross-sectional dimension than in another surrounding region, whereby with the swivel lug received in the swivel recess and with the swivel/lock region and the swivel bracket element swiveled out of the insertion-relative position relative to each other, the swivel lug cannot be moved out of the swivel recess.

8. The device according to claim 6,
wherein on the swivel bracket element, two swivel lugs extending substantially along a common swivel axis are provided, the swivel/lock region of the guideway element being designed in a fork shape with two forked end regions and having a swivel recess in each forked end region.

9. The device according to claim 1,
wherein on the swivel bracket element, at least one locking lug is provided, and the swivel/lock region assembly of the guideway element, a locking recess open in a surrounding region being provided in assignment to each locking lug for the insertion of the locking lug.

10. The device according to claim 9,
wherein the at least one locking lug is movable in a direction of a projection axis between a receiving position for insertion into a locking recess and a locking position, whereby in the locking position, a locking section of the locking lug engages an opposing locking section of the locking recess such that the locking lug cannot be moved out of the locking recess.

11. The device according to claim 10,
wherein the at least one locking lug is pre-tensioned in its locking position.

12. The device according to claim 10,
wherein on the swivel carrier element, two locking lugs extending along a common longitudinal projection axis are provided, and that on a swivel/lock region of the guideway element two locking-recess projections are provided, each having a locking recess.

13. The device according to claim 9,
wherein said at least one locking lug is provided on the swivel carrier element.

14. The device according to claim 1,
wherein the optics carrier arrangement includes the guideway region positionable at the proximal end of the tubular device body with a first guide element that surrounds the longitudinal axis of the tubular device body, and having on the optics carrier, a second guide element, that is guided to move the optics carrier along its path of motion about the longitudinal axis of the tubular device body along the first guide element.

15. The device according to claim 14,
wherein the first guide element comprises a guide groove and the second guide element a guide projection, whereby the guide groove for the engagement of the guide projection is open from the proximal end region of the device body in the direction of the longitudinal axis of the tubular device body.

16. The device according to claim 15,
wherein the guide groove has a groove undercut region and that on the guide projection an undercut engagement region is provided that engages the groove undercut region.

17. The device according to claim 14,
wherein the first guide element comprises a guide surface and the second guide element a guide ring, whereby the guide ring has an opposing guide surface to abut the guide surface.

18. The device according to claim 17,
wherein one surface of the guide surface and opposing guide surface is an internal circumferential surface and the other surface an external circumferential surface.

19. The device according to claim 17,
wherein in assignment to one surface of guide surface and opposing guide surface a guide recess is provided that extends in a direction of the path of motion and in assignment to the other surface, a guide projection extending in the direction of the path of motion is assigned for engagement in the guide recess.

20. The device according to claim 17, wherein the guide ring is radially elastic.

21. The device according to claim 17,
wherein in the region of the proximal end of the tubular device body an additional guide surface is provided that circularly encloses the longitudinal axis of the tubular device body, and that on the guide ring, an additional opposing guide surface is provided to abut the additional guide surface.

22. The device according to claim 14,
wherein one of the guideway region and the optics carrier comprises a fixing element that can be pressed against the other of the guideway region and the optics carrier.

23. The device according to claim 22,
wherein on the optics carrier, a fixing element is provided that can be pressed, in relation to the longitudinal tubular axis of the tubular device body, substantially radially from the outside against an abutment region on the guideway region.

24. The device according to claim 23,
wherein in order to produce and release the fixation, the fixing element is movable substantially radially relative to the longitudinal axis of the tubular device body.

25. The device according to claim 22,
wherein the fixing element is assigned a fixing element actuator for moving the fixing element between a fixed position and a released position.

26. The device according to claim 25,
wherein the fixing element actuator comprises, on a impingement component, a first impingement region that is movable with the fixing element and a second impingement region that impinges the first impingement region and can be displaced to move the fixing element relative to the first impingement region, whereby at least one impingement region is wedge-shaped.

27. The device according to claim 26,
wherein the first impingement region with the fixing element is displaceable in a first direction of displacement and that the second impingement region with the impingement component is displaceable in an angled, second direction of displacement in relation to the first direction of displacement.

28. The device according to claim 27,
wherein the second impingement region with the impingement component is displaceable in a substantially orthogonal-second direction of displacement in relation to the first direction of displacement.

29. The device according to claim 26, wherein the impingement component is assigned a spindle drive.

30. The device according to one of the claim 26, wherein the first impingement region and the second impingement region have a positive lock with one another.

31. The device according to claim 26, wherein each impingement region is wedge-shaped.

32. The device according to claim 1, wherein on the optics carrier an optics fixation region is provided for fixing an optics system on the optics carrier.

33. The device according to claim 32, wherein the optics fixation region comprises, on the optics carrier, a dovetail interior profile or a dovetail exterior profile, as well as a movable optics system fixing element for producing and releasing the fixation of the optics system relative to the optics carrier.

* * * * *